United States Patent
Rinehart et al.

[11] Patent Number: 6,156,724
[45] Date of Patent: *Dec. 5, 2000

[54] USES OF DIDEMNINS AS IMMUNOMODULATING AGENTS

[76] Inventors: Kenneth L. Rinehart, 1306 S. Carle Ave., Urbana, Ill. 61801; Glynn Faircloth, 26 Lansdowne St., Cambridge, Mass. 02139

[*] Notice: This patent issued on a continued prosecution application filed under 37 CFR 1.53(d), and is subject to the twenty year patent term provisions of 35 U.S.C. 154(a)(2).

[21] Appl. No.: 09/111,190

[22] Filed: Jul. 7, 1998

Related U.S. Application Data

[63] Continuation of application No. 08/664,234, Jun. 7, 1996, abandoned.

[51] Int. Cl.$^7$ ............................................. A61K 38/12
[52] U.S. Cl. ........................... 514/10; 514/9; 514/11
[58] Field of Search ........................... 514/413, 9, 10, 514/11

[56] References Cited

U.S. PATENT DOCUMENTS

| | | | |
|---|---|---|---|
| 4,493,796 | 1/1985 | Rinehart, Jr. | 260/112.5 |
| 4,548,814 | 10/1985 | Rinehart, Jr. | 424/95 |
| 4,782,135 | 11/1988 | Rinehart, Jr. | 530/317 |
| 4,948,791 | 8/1990 | Rinehart, Jr. et al. | 514/183 |
| 4,950,649 | 8/1990 | Rinehart | 514/10 |
| 5,137,870 | 8/1992 | Rinehart | 514/10 |
| 5,294,603 | 3/1994 | Rinehart | 514/10 |
| 5,294,604 | 3/1994 | Nussenblatt et al. | 514/11 |

*Primary Examiner*—William R. A. Jarvis
*Attorney, Agent, or Firm*—Ernest V. Linek; Banner & Witcoff, Ltd.

[57] ABSTRACT

The present invention is based upon the immunomodulatory activity of synthetic and semi-synthetic didemnin compounds. It has surprisingly been discovered that certain didemnin compounds possess unexpectedly high immunomodulation activity, and thus will be useful for modulating or regulating immunological functions in warm blooded animals. From the data provided herein it is believed that the physician will be able to determine the appropriate dosage of the immunosuppressant didemnins of the present invention. The actual dosage to be administered depends, inter alia, on the animal species to be treated, the subject animal's size, and the capacity of the subject to utilize the particular didemnin compound administered. Accordingly, the actual amounts of any didemnin compound required to be administered depend on the judgment of the practitioner.

4 Claims, No Drawings

USES OF DIDEMNINS AS IMMUNOMODULATING AGENTS

This application is a continuation of Ser. No. 08/664,234, filed Jun. 7, 1996, now abandoned.

STATEMENT OF GOVERNMENT SUPPORT

Support for this invention was received from the National Institute of Allergy and Infectious Diseases under Grant No. AI 04769 and the National Institute of General Medical Sciences under Grant No. GM 27029. Thus the government of the United States of America has certain rights in this invention.

BACKGROUND OF THE INVENTION

The didemnins, marine organism-derived cyclic depsipeptides, were isolated from the Caribbean tunicate *Trididemnum solidum* by Rinehart et al. as antitumor and antiviral reagents[3-5] and numerous biological studies on didemnins have been conducted.[6,7] In in vitro studies, didemnin B (DB, shown below as Compound 1, hereafter, 1), one of the most potent components, was cytotoxic to L1210 murine leukemia cells at very low concentrations, and to CV-1 monkey kidney cells at much higher concentrations.[3]

reported that didemnin B inhibits protein synthesis by stabilizing aminoacyl-tRNA binding to the ribosomal A-site, preventing translocation but not peptide bond formation.[11a] Most recently, didemnin B has been reported to induce apoptosis in human HL-60) cells at the most rapid rate yet recorded.[11d]

Both didemnins A (shown above as Compound 2, hereafter, DA, or 2) and B (1) have been shown to be strong inhibitors of various viruses in vitro.[3,12] Compounds 1 and 2 also showed activity in vitro against strains of the lethal RNA viruses Venezuelan equine encephalomyelitis, yellow fever, sandfly fever, Rift Valley fever and a Pichinde virus, for all of which no effective chemotherapeutic agents exist.[13] In vivo, 1 protected 90% of Rift Valley fever virus-infected mice, although considerable toxicity to the host animal was observed.[5,13]

In vivo testing, of 1 and 2 against herpes simplex virus-2 (HSV-2) in mice has shown some efficacy in topical administration, but intracranial administration against encephalitis HSV-1, subcutaneous administration against Semliki-Forest virus, and cutaneous application against HSV-1 failed because of narrow therapeutic indexes.[5,12] On the whole, the high toxicity of 1 and 2 precludes their use as antiviral agents.

Didemnin B (1) inhibited lymphocyte blastogenesis and the mixed lymphocyte reaction (MLR) in vitro in murine cells,[14] requiring lower concentrations than cyclosporin A tested in a human lymphocyte system.[15] Some efficacy was observed in the graft-vs-host (GVH) reaction in mice and allograft transplantation in a rat with an auxiliary heart graft after treatment with.[14,16]

In in vivo studies, 1 was effective in P388 and B16 murine tumor models and in a Yoshida ascites model.[3,8] Compound 1 was the first marine-derived compound to be evaluated in Phase I and Phase II clinical trials by the National Cancer Institute. As an antitumor agent[9] it has shown complete or partial response in previously treated non-Hodgkins lymphomas.[10] Inhibition of protein synthesis and, to a lesser extent, DNA synthesis were earlier proposed as the mode of action for the cytotoxicity of the didemnins.[11a] Recently, Crews, et al. reported purification of a didemnin-binding protein from a bovine brain homogenate which appeared to be identical to human translational elongation factor-1α (EF-1α) by affinity chromatography using N-biotinylbis(ε-aminocaproyl)didemnin A as a ligand. Didemnin A binds to EF-1α in a GTP-dependent manner, i.e., it binds to the GTP-EF-1α complex, but does not inhibit EF-1α's GTPase activity.[11a] More recently, SirDeshpande and Toogood have While 1 has shown a remarkable spectrum of biological activities, each has been accompanied by considerable toxicity.

Hence, modifications of the compound to increase a specific bioactivity while attenuating its general toxicity is a worthy endeavor.

Rinehart et al. have previously reported some structural modifications and structure-activity relationships (SAR's) of didemnins.[7] These preliminary results revealed that simple acylation of the N-terminus of didemnin A enhanced activities dramatically.[3c,7] Several limited SAR studies of didemnins have been recently reported by others. Jouin and co-workers reported a total synthesis of nordidemnin B and four nordidemnin congeners and their in vitro and in vivo activities: mandelyl-Pro-,(p-hydroxyphenyl)propionyl-Pro-, and palmityl-Pro-nordidemnin A, and [L-MeLeu$^7$] nordidemnin B.[17] Kessler and co-workers reported the preparation and solution structure of [L-MeLeu$^7$]-didemnin B.[18] Most recently Joullie and co-workers reported synthesis and bioactivity of didemnin B congeners: [dehydro-L-Pro$^8$] and [trans-4-hydroxyPro$^8$] DB, and dehydro-L-Pro-DA and trans-4-hydroxyPro-DA as well as L-Pro-DA.[19] The biological results can be summarized as follows: mandelyl-Pro-norDA, (p-hydroxyphenyl)-propionyl-Pro-nor DA, and [dehydroPro)$^8$] analogues showed comparable activity to 1, but trans-4-hydroxyPro$^8$ analogues showed somewhat weaker cytotoxicity than that of DB. Palmityl-Pro-norDA and [L-MeLeu$^7$] congeners had significantly diminished activity in the inhibition of tumor cell growth. The [dehydroPro$^8$] analogues showed comparable antiproliferative activity in an in vitro immunosuppressive assay.[19]

Numerous natural and semi-synthetic didemnin compounds have been reported in patents. See for example, U.S. Pat. No. 4,948,791; U.S. Pat. No. 5,137,870; U.S. Pat. No. 5,294,603; U.S. Pat. No. 4,782,135; U.S. Pat. No. 4,493,796; U.S. Pat. No. 4,548,814; U.S. Pat. No. 4,950,649; the disclosures of which are hereby incorporated herein by reference.

The term "immunomodulation" denotes an intended physical or chemical alteration in the function of a host's immune system. The distinction is made between manipulations which cause a decrease and others which cause an increase in number and/or function of immune mechanisms. The desire and necessity to artificially control immune responses were born during the advent of clinical transplantations in the years 1 965–75 when the immunologists were faced with the daunting task of preventing graft rejections. Hence was born the era of "Biological Response Modifiers (BRM's)" which can be classed as either immunosuppressive or immunostimulatory. A special subgroup of the latter exerts its stimulatory effects only on defective immune mechanisms and directs them towards normalization. Such substances are termed "immune restorative agents".

In the past, living and attenuated micro-organisms, autologous and heterologous proteins and injections of animal organ preparations were used with the aim of restoring an impaired defense mechanism. At present, thymic peptides, synthetic low molecular weight compounds, chemically modified nucleotides, polysaccharides from fungi and, especially, some plant extracts are also used for the same purpose.

The recently renewed interest in the immunomodulators arose from their potential therapeutic use in several clinical situations including: (a) chronic bacterial and/or viral infections; (b) immune dysfunction; (c) immune deficiency syndromes; and (d) tumors. Although an extensive search for plant derived natural products with immunostimulatory/immunosuppressive activities is currently under way, very few such substances have entered the market.

SUMMARY OF THE INVENTION

The present invention is based upon the immunomodulatory activity of synthetic and semi-synthetic didemnin compounds. Immunomodulation is a developing segment of immuno-pharmacology. Immunomodulator compounds and compositions, as the name implies, are useful for modulating or regulating immunological functions in warm blooded animals. Immunomodulators may be immunostimulants for building up immunities to or initiate healing of certain diseases and disorders. Conversely, they may be immunoinhibitors or immunosuppressors for preventing undesirable immuno-reactions of the body, e.g., to foreign materials and/or autoimmune diseases.

Immunomodulators have been found to be useful for treating systemic autoimmune diseases, such as lupus erythematosus, as well as immunodeficiency diseases. Further, immunomodulators may be useful for immunotherapy of cancer or to prevent rejections of foreign organs or other tissues in transplants, e.g., kidney, heart or bone marrow.

Various immunomodulator compounds have been discovered including muramylic acid dipeptide derivatives, levamisole, niridazole, oxysuran, flagyl and others from the groups of interferons, interleukins, leukotrienes, corticosteroids and cyclosporins. Many of these compounds have been found, however, to have undesirable side effects and/or high toxicity. Thus, doses are typically kept low (and may include delivery in a time release formulation) and one or more compounds may be administered to patients in need of such treatment. One such class of additive agents are the antiproliferative agents. Such agents include azathioprine, brequinar sodium, deoxyspergualin, mizaribine, mycophenolic acid morpholino ester, cyclosporin, and FK-506.

New immunomodulator compounds are therefore needed to provide a wider range of immunomodulator function for specific areas with a minimum of undesirable side effects. The didemnin compounds of the present invention represent yet another advance in this area.

Typical uses of the immunomodulator compounds of the following invention include the following:

(a) Suppression of graft rejections in mammals, particularly in humans. This activity may be accomplished by administering to the patient a composition comprising an immunosuppressant compound, in a physiologically acceptable vehicle, in an amount effective to reduce or eliminate the undesirable immune response. This activity is especially important when the graft rejection results from a bone marrow or organ transplant.

(b) Preventing or significantly reducing the autoimmune response in a mammal, particularly in humans. This activity may be accomplished by administering to the patient a composition comprising an immunosuppressant compound, in a physiologically acceptable vehicle, in an amount effective to reduce or eliminate an immune response.

(c) Treating mammals, particularly humans, having a disease state that is alleviated or ameliorated by treatment with an immunosuppressant compound. This activity may be accomplished by administering to the patient a therapeutically effective amount of an immunosuppressive compound. Disease states which are amenable to this treatment include, but are not limited to; treating rheumatoid arthritis; treating graft vs. host disease (xenograft or allograft), and organ transplant rejection; treating disorders involving undesirable or inappropriate complement activity such as soft tissue destruction (e.g., due to burns), myocardial infarct induced trauma, adult respiratory distress syndrome, and myocardial ischemia and re-perfusion; specific and non-specific proteolytic processing of C5; inflammation associated with kidney stones, systemic lupus erythematosus, nephrotoxic glomeronephritis, and multiple sclerosis; atrophic gastritis, thyroiditis, allergic encephalomyelitis, gastric mucosa, thyrotoxicosis, autoimmune hemolytic anemia, pemphigus vulgaris, sympathetic ophthalmia, delayed-type hypersensitivity, autoimmune disorders and drug allergies; and tissue plasminogen activator therapy and cardiopulmonary bypass.

(d) Treating humans suffering from multiple sclerosis. This activity may be accomplished by administering to the patient a composition containing a therapeutically effective dose of an immunosuppressive compound dissolved or dispersed in a physiologically tolerable carrier.

(e) Treating humans suffering from arthritis, or similar inflammatory diseases, to control the delayed type hypersensitivity reaction, or of the inflammatory process associated with rejection of organ transplant in a warm-blooded animal. These activities may be accomplished by administering to the patient a therapeutically effective amount of at least one immunomodulating agent in an amount effective to alleviate the disease state, at least temporarily.

(f) Treating mammals, particularly humans, suffering from hyperplasia of the epidermis resulting from a T-lymphocyte mediated immune response in the mammal (e.g., psoriasis). This activity may be accomplished by administering an immunomodulating compound in a physiologically acceptable vehicle to an afflicted site on the mammal, thereby suppressing a T-lymphocyte mediated immune response associated with psoriasis. Such treatment can be topical, i.e., whereby the immunomodulating compound is administered as a cream, ointment or solution. Alternatively (or additionally) the compound may be administered orally, intravenously, or parenterally. In addition to treating psoriasis, this method is also suitable for the alleviation and/or amelioration of contact dermatitis and symptoms associated therewith resulting.

(g) Treating mammals, particularly humans, suffering chronic inflammatory conditions, including for example, chronic arthritis, periodontitis, gingivitis, granulomas and fibrosis. This activity may be accomplished by administering an effective amount of an immunomodulating compound to the patient, in an amount effective to ameliorate or alleviate the symptoms of said chronic inflammatory condition.

(h) Treating mammals, particularly humans, suffering from joint diseases, exhibiting symptoms of inflammation, tissue swelling, and bone and cartilage degradation. This activity may be accomplished by administering an effective amount of an immunomodulating compound to the patient.

DETAILED DESCRIPTION OF THE PREFERRED EMBODIMENTS

Evaluation of Immunomodulatory Activities of the Didemnins

The present invention is based upon the comprehensive study of the bioactivities of 42 didemnin congeners (see Table 1 below), either isolated from the marine tunicates *Trididemnum solidum* and *Aplidium albicans* or prepared synthetically and semi-synthetically. Immunosuppressive activity of these didemnins was determined using a mixed lymphocyte reaction (MLR) assay. These assays revealed that the native cyclic depsipeptide core is an essential structural requirement for most of the bioactivities of the didemnins, especially for cytotoxicities and antiviral activities. The linear side-chain portion of the peptide can be altered with a gain, in some cases, of bioactivities. In particular, dehydrodidemnin B, tested against several types of tumor cells and in in vivo studies in mice, as well as didemnin M, tested for the mixed lymphocyte reaction and graft vs. host reaction in murine systems, showed remarkable gains in their in vitro and in vivo activities compared to didemnin B.

The immunology data suggest that the immunosuppressive activity of didemnins is mediated mostly by cytotoxicity to lymphoblasts occurring at a later stage of activation in the cell-mediated immune response, except for some glutaminyl didemnins, 37–39, and acyclo-DA (17), as indicated by the relatively constant therapeutic index utilizing cytotoxicity data to proliferating lymphoblasts versus resting lymphocytes. These results indicate that the immunosuppressive activity of didemnins is, in most cases, a result of antiproliferation of stimulated T-cells, as demonstrated for 1 by others.[36] In the cases of 37–39 and 17, however, some unique or specific mechanisms of action such as those seen in cyclosporin A,[37] FK 506 or rapamycin[38] may be involved in the immunosuppressive actions (e.g., non-cytotoxic immunosuppression during early stage events involving T-cell activation).

TABLE 1

Structures and Some Physical Properties of Didemnins

| didemnins | # | formula[b] | HPLC T_R min(solvent)[c] | $[\alpha]_D$ in CHCl$_3$ (temp., conc.) | within the ring 1st[2] | within the ring Hip[3] | within the ring Me$_2$Tyr[5] | linear peptide N[a] (8) | linear peptide 9 | glutaminyl 10-15 | ref. |
|---|---|---|---|---|---|---|---|---|---|---|---|
| Didemnin A (DA) Lead | 2 | C$_{49}$H$_{78}$N$_6$O$_{12}$ | 17.0 (E) | −136° (25, 7.50)[d] | 1st | Hip | Me$_2$Tyr | H | | | 3a |
| Didemnin B (DB) Lead | 1 | C$_{57}$H$_{89}$N$_7$O$_{15}$ | 26.8 (A) | −78° (25, 6.91)[d] | 1st | Hip | Me$_2$Tyr | Pro | | | 3a |
| Z-DA | 3 | C$_{57}$H$_{84}$N$_6$O$_{14}$ | 36.8 (A) | −98° (26, 0.96) | 1st | Hip | Me$_2$Tyr | Z | | | 23 |
| Z-[3R,4R,5S-1st[2]]DA | 4 | C$_{57}$H$_{84}$N$_6$O$_{14}$ | 36.0 (A) | −14° (25, 0.16) | 3R,4R,5S-1st[e] | Hip | Me$_2$Tyr | Z | | | f |
| Z-[3S,4R,5R-1st[2]]DA | 5 | C$_{57}$H$_{84}$N$_6$O$_{14}$ | 35.6 (A) | −102° (25, 0.11) | 3S,4R,5R-1st[e] | Hip | Me$_2$Tyr | Z | | | f |
| Z-[3S,4S,5S-1st[2]]DA | 6 | C$_{57}$H$_{84}$N$_6$O$_{14}$ | 43.8 (A) | −28° (25, 0.11) | 3S,4S,5S-1st[e] | Hip | Me$_2$Tyr | Z | | | f |
| O-Acetyl DA | 7 | C$_{51}$H$_{80}$N$_6$O$_{13}$ | 24.4 (A) | −136° (24, 0.38) | O-Acetyl-1st[e] | Hip | Me$_2$Tyr | H | | | f |
| [Phth-Ala$^9$]DB | 8 | C$_{65}$H$_{92}$N$_8$O$_{16}$ | 31.4 (A) | −32° (25, 0.11) | 1st | Hip | Me$_2$Tyr | Pro | Phth-Ala[e] | | 20 |
| [Anhydro1st[2]][Phth-Ala$^9$]DB | 9 | C$_{65}$H$_{90}$N$_8$O$_{15}$ | 41.2 (A) | −20° (28, 0.07) | Anhydro1st[e] | Hip | Me$_2$Tyr | Pro | Phth-Ala[e] | | 20 |
| [H$_2$-Hip$^3$]DA | 10 | C$_{49}$H$_{80}$N$_6$O$_{12}$ | 27.0 (E) | −91° (28, 0.26) | 1st | H$_2$-Hip[d] | Me$_2$Tyr | H | | | f |
| [Hip$^3$ oxime]DB | 11 | C$_{57}$H$_{90}$N$_8$O$_{14}$ | 22.4 (A) | −82° (22, 0.24) | 1st | Hipoxime[d] | Me$_2$Tyr | Pro | | | f |
| epiHip$^3$]DA | 12 | C$_{49}$H$_{78}$N$_6$O$_{12}$ | g | −100° (23, 0.13) | 1st | epiHip[d] | Me$_2$Tyr | H | | | f |
| [Tyr$^5$]DB (Didemnin N) | 13 | C$_{55}$H$_{85}$N$_7$O$_{15}$ | 18.0 (A) | 54° (24, 0.13) | 1st | Hip | Tyr | Pro | | | 20 |
| [IodoMe$_2$Tyr$^5$]DB | 14 | C$_{57}$H$_{88}$IN$_7$O$_{15}$ | 26.5 (A) | −74° (22, 0.17) | 1st | Hip | IodoMe$_2$Tyr[d] | Pro | | | f |
| [H$_6$-Me$_2$Tyr$^5$]DB | 15 | C$_{57}$H$_{95}$N$_7$O$_{15}$ | 22.2 (B) | −29° (23, 0.41) | 1st | Hip | H$_6$—Me$_2$Tyr[d] | Pro | | | f |
| [H$_6$-NMePhe$^5$]DB | 16 | C$_{57}$H$_{94}$N$_7$O$_{14}$ | 26.5 (B) | −29° (24, 0.41) | 1st | Hip | H$_6$-NMePhe[d] | Pro | | | f |
| N[a]-Acetyl DA | 18 | C$_{51}$H$_{80}$N$_6$O$_{13}$ | 22.2 (A) | −81° (24, 1.1) | 1st | Hip | Me$_2$Tyr | n-CH$_3$CO— | | | f |
| N[a]-Propionyl DA | 19 | C$_{52}$H$_{82}$N$_6$O$_{13}$ | 25.2 (A) | −74° (24, 0.90) | 1st | Hip | Me$_2$Tyr | n-CH$_3$CH$_2$—CO— | | | f |
| N[a]-n-Butyryl DA | 20 | C$_{53}$H$_{84}$N$_6$O$_{13}$ | 23.8 (B) | −88° (24, 0.26) | 1st | Hip | Me$_2$Tyr | n-CH$_3$(CH$_2$)$_2$—CO— | | | f |
| N[a]-Pentanoyl DA | 21 | C$_{54}$H$_{86}$N$_6$O$_{13}$ | 26.8 (B) | −71° (24, 0.33) | 1st | Hip | Me$_2$Tyr | n-CH$_3$(CH$_2$)$_3$—CO— | | | f |
| N[a]-Hexanoyl DA | 22 | C$_{55}$H$_{88}$N$_6$O$_{13}$ | 29.6 (B) | −94° (24, 0.10) | 1st | Hip | Me$_2$Tyr | n-CH$_3$(CH$_2$)$_4$—CO— | | | f |
| N[a]-Octanoyl DA | 23 | C$_{57}$H$_{92}$N$_6$O$_{13}$ | 40.4 (B) | −71° (24, 0.32) | 1st | Hip | Me$_2$Tyr | n-CH$_3$(CH$_2$)$_6$—CO— | | | f |
| N[a]-Dodecanoyl DA | 24 | C$_{61}$H$_{100}$N$_6$O$_{13}$ | 30.6 (C) | −64° (24, 0.33) | 1st | Hip | Me$_2$Tyr | n-CH$_3$(CH$_2$)$_{10}$—CO— | | | f |
| N[a]-Octadecanoyl DA | 25 | C$_{67}$H$_{112}$N$_6$O$_{13}$ | 25.0 (D) | −73° (24, 0.17) | 1st | Hip | Me$_2$Tyr | n-CH$_3$(CH$_2$)$_{16}$—CO— | | | f |
| Didemnin G (N[a]-Formyl DA) | 26 | C$_{50}$H$_{78}$N$_6$O$_{14}$ | 27.2 (A) | −94° (28, 0.10) | 1st | Hip | Me$_2$Tyr | CHO | | | 4b |
| N[a]-Leucyl DA | 27 | C$_{55}$H$_{89}$N$_7$O$_{13}$ | 25.6 (E) | −54° (28, 0.17) | 1st | Hip | Me$_2$Tyr | Leu | H | | f |
| N[a]-Prolyl DA | 28 | C$_{54}$H$_{85}$N$_7$O$_{13}$ | 26.6 (E) | −73° (28, 0.18) | 1st | Hip | Me$_2$Tyr | Pro | H | | f |
| N[a]-D-Prolyl DA | 29 | C$_{54}$H$_{85}$N$_7$O$_{13}$ | 25.2 (E) | −70° (25, 0.65) | 1st | Hip | Me$_2$Tyr | D-Pro | H | | f |
| [Pyruvyl$^9$]DB (dehydrodidemnin B) | 30 | C$_{57}$H$_{87}$N$_7$O$_{15}$ | 24.0/25.2 (A)[h] | −69° (28, 0.45) | 1st | Hip | Me$_2$Tyr | Pro | Pyruvyl | | 2f |
| [Acetyl$^9$]DB | 31 | C$_{56}$H$_{87}$N$_7$O$_{15}$ | 26.4 (A) | −85° (24, 1.6) | 1st | Hip | Me$_2$Tyr | Pro | CH$_3$CO— | | f |
| [Propionyl$^9$]DB | 32 | C$_{57}$H$_{89}$N$_7$O$_{14}$ | 28.6 (A) | −77° (25, 2.9) | 1st | Hip | Me$_2$Tyr | Pro | CH$_3$CH$_2$CO— | | f |
| [Isobutyryl$^9$]DB | 33 | C$_{58}$H$_{91}$N$_7$O$_{14}$ | 30.8 (A) | −90° (25, 0.15) | 1st | Hip | Me$_2$Tyr | Pro | Isobutyryl | | f |
| [Isobutyryl$^9$-D-Pro$^5$]DB | 34 | C$_{58}$H$_{91}$N$_7$O$_{14}$ | 28.4 (A) | −69° (25, 0.89) | 1st | Hip | Me$_2$Tyr | D-Pro | Isobutyryl | | f |
| [Ala$^8$]DB | 35 | C$_{55}$H$_{87}$N$_7$O$_{15}$ | 21.4 (A) | −120° (26, 1.3) | 1st | Hip | Me$_2$Tyr | Ala | L-Lac | | f |
| [D-Pro$^8$]DB | 36 | C$_{57}$H$_{89}$N$_7$O$_{15}$ | 22.4 (A) | −66° (25, 1.2) | 1st | Hip | Me$_2$Tyr | D-Pro | L-Lac | | f |
| O-pGlu DB | 37 | C$_{62}$H$_{94}$N$_8$O$_{17}$ | 23.4 (A) | −79° (20, 1.4) | 1st | Hip | Me$_2$Tyr | Pro | L-Lac | pGlu[e] | f |
| Didemnin M | 38 | C$_{67}$H$_{102}$N$_{10}$O$_{19}$ | 19.8 (A) | −68° (25, 1.1) | 1st | Hip | Me$_2$Tyr | Pro | L-Lac | pGlu-Gln-[e] | 20 |
| Didemnin E | 39 | C$_{72}$H$_{110}$N$_{12}$O$_{21}$ | 14° (25, 0.16) | 18.0 (A) | 1st | Hip | Me$_2$Tyr | Pro | L-Lac | pGlu-(Gln)$_2$-[e] | 4a |
| Didemnin D | 40 | C$_{77}$H$_{118}$N$_{14}$O$_{23}$ | 19.0 (A) | −14° (25, 0.16) | 1st | Hip | Me$_2$Tyr | Pro | L-Lac | pGlu-(Gln)$_3$-[e] | 4a |
| Didemnin X | 41 | C$_{82}$H$_{131}$N$_{13}$O$_{23}$ | 28.4 (A) | −65° (20, 0.93) | 1st | Hip | Me$_2$Tyr | Pro | L-Lac | Hydec-(Gln)$_3$-[e] | 20 |
| Didemnin Y | 52 | C$_{87}$H$_{139}$N$_{15}$O$_{25}$ | 25.4 (A) | −89° (20, 0.63)[j] | 1st | Hip | Me$_2$Tyr | Pro | L-Lac | Hydec-(Gln)$_4$-[e] | 20 |
| Acyclodidemnin A[d] | 17 | C$_{49}$H$_{80}$N$_6$O$_{13}$ | 16.1 (E) | −70° (26, 0.06) | 1st | Hip | Me$_2$Tyr | Pro | | | 20 |

TABLE 1-continued

Structures and Some Physical Properties of Didemnins

| didemnins | # | formula[b] | HPLC T$_R$ min(solvent)[c] | $[\alpha]_D$ in CHCl$_3$ (temp., conc.) | modified sites (indicated by bold face)[a] | | | | | ref. |
|---|---|---|---|---|---|---|---|---|---|---|
| | | | | | within the ring | | | linear peptide | glutaminyl | |
| | | | | | 1st[2] | Hip[3] | Me$_2$Tyr[6] | N$^a$(8) | 10–15 | |

[a]Structures of unusual subunits are shown in Chart 2. Superscripts indicate unit modified, substituted, or added.
[b]Based on HRFAB data (Δ within 4 mDa).
[c]Solvent Systems (RP C-18 column): A = 7:1 MeOH—H$_2$O, B = 8:1 MeOH—H$_2$O, C = 12:1 MeOH—H$_2$O, D = MeOH, E = 7:1 MeOH-0.1M NaCl.
[d]CH$_2$Cl$_2$.
[e]Structure is shown in Chart 2.
[f]Present work.
[g]R$_f$ = 0.13 (15:1 CHCl$_3$—MeOH, silica-gel, where R$_f$ = 0.23 for DA (HPLC data not available).
[h]Two peaks appeared due to conformers.[21]
[i]Measured in 4:1 CHCl$_3$—MeOH.

A total of fifteen didemnin analogues isolated by Rinehart et al. from extracts of the Caribbean tunicate *T. solidum* have been characterized.[2,3,20] Of these, eleven congeners (1, 2, 12, 13, 17, 26 and 38–42) are evaluated herein. Additionally, [pyruvyl[9]] DB (dehydrodidemnin B, 30), recently isolated from the Mediterranean tunicate *A. albicans*, was also tested.[21] Didemnin A (2) has the basic structure common to many other congeners, consisting of a cyclic depsihexapeptide with a D-N-methylleucine (D-MeLeu) side chain attached to $Thr^1$.

Compound 2 (DA) was used as the starting material in the preparation of twenty congeners since its N-terminus, a free secondary amino group, offers a site to attach various acyl groups to the cyclic depsipeptide. Didemnin B (1), which has a Lac-Pro-acyl unit attached to the N-terminus of 2, was also used as a starting molecule for some semisynthetic modifications.

Congeners with the Cyclic Depsipeptide Modified
The Isostatine[2] Subunit.

One of the most unusual subunits, isostatine (Ist), is an intriguing target site for modifications. During the total synthesis of the didemnins, all eight possible stereoisomers of Ist were synthesized,[22] and selected stereoisomers have been incorporated into the cyclic backbone of the peptide to observe the effects of the stereochemistry of Ist on bioactivities. Since Z-didemnin A (3) is known to possess more potent bioactivities than 2 itself,[1,6,7] bioactivities of three compounds varying in a single stereocenter, Z-[3R,4R,5S-Ist[2]]-, Z-[3S,4S,5S-Ist2]-, and Z-[3S,4S,5R-Ist[2]]-didemnins A, compounds 4, 5, and 6, respectively, were compared. These compounds were prepared following the method used in the total synthesis of 2, which contains [3S,4R,5S-$Ist^2$] (see, Scheme 1, below)[23]

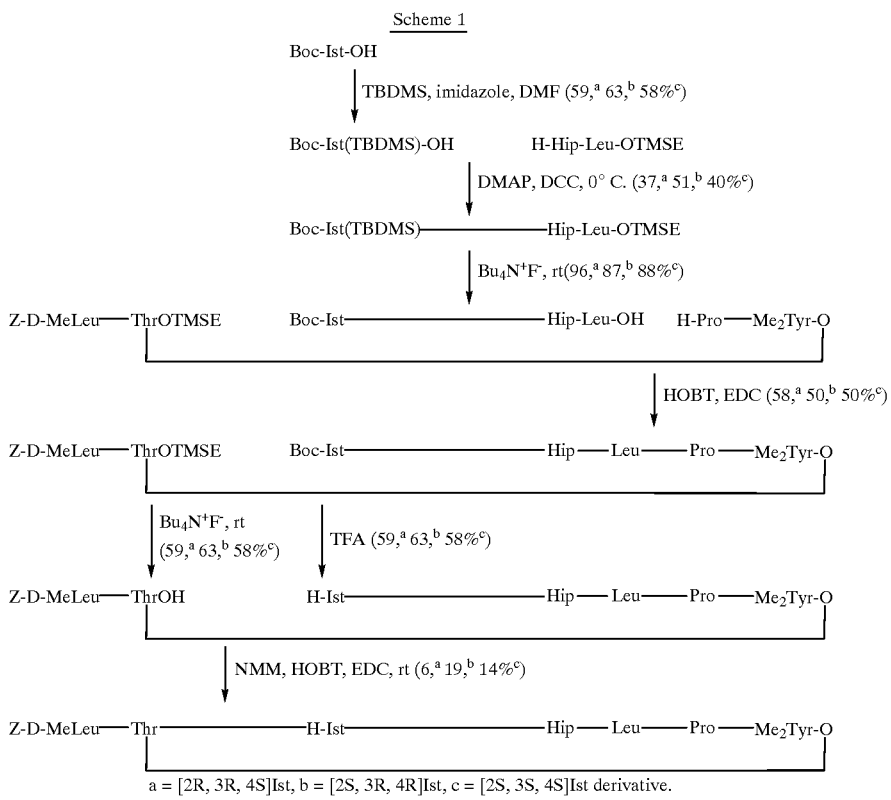

a = [2R, 3R, 4S]Ist, b = [2S, 3R, 4R]Ist, c = [2S, 3S, 4S]Ist derivative.

The hydroxyl group at the C-3 position of $Ist^2$ was also modified. Z-Didemnin A (3) was acetylated, and hydrogenolysis of N-Z-O-acetyl-[$Ist^2$]didemnin A afforded O-acetyl[$Ist^2$]didemnin A (7).

Treatment of 1 with phthalimide, diethyl azodicarboxylate (DEAD), and $PPh_3$ gave two products, 8 ([Phth-Ala[9]] DB) and an anhydro byproduct, 6 ([Anhydro-$Ist^2$][Phthal-Ala[9]]DB) which has a trans-2,3-olefin in the $Ist^2$ unit.[20,24]
The $Hip^3$ Subunit The Hip (hydroxisovalerylpropionyl) subunit is also an important modification site of the didemnins. It has been proposed that the keto group of the Hip unit plays a major role in the bioactivities of didemnins.[4a] Treatment of 2 with $NaBH_4$ afforded the reduced Hip analogue, [(2S,3R,4S)-$H_2$-$Hip^3$]didemnin A (=[$H_2Hip^3$]DA, 10)[41,20] as major product.

Treatment of 1 with hydroxylamine gave [$Hip^3$oxime] didemnin B (11). Epididemnin $A_1$ (=[H-epi$Hip^3$]DA, 12) from *T. solidum* contains a (2S,4R)-hydroxyisovalerylpropionyl (Hip) residue in place of (2S,4S)-Hip in 1.[20]

Me$_2$Tyr$^6$ Subunit

Didemnin N (=[Tyr$^6$]DB, 13), isolated from *T. solidum*, has tyrosine (Tyr) in place of the N,O-dimethyltyrosine (Me$^2$Tyr) of 1.[20] Several chemical modifications of the Tyr unit were carried out. See Scheme 2 below for structures.

In connection with the present invention, various fatty acids were condensed with the N-terminus of 2 to evaluate the effects of lipophilicity and size of the acyl side chain on the activities. Compounds semisynthetically prepared include N$^\alpha$-propionyldidemnin A (19), N$^\alpha$-n-

SCHEME 2

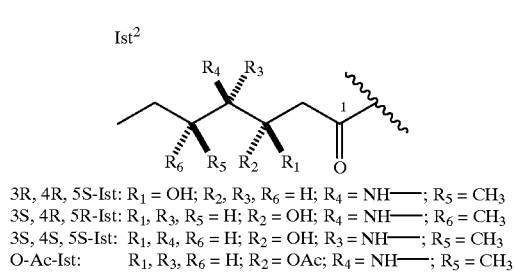
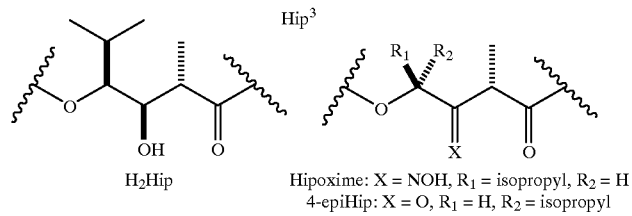
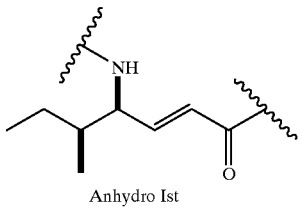
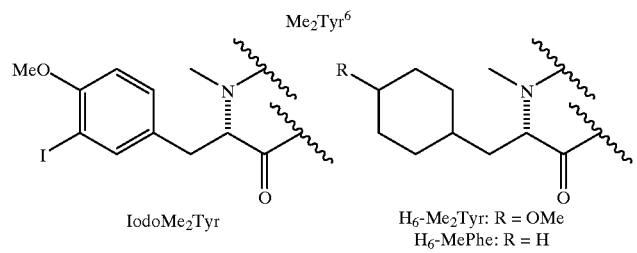
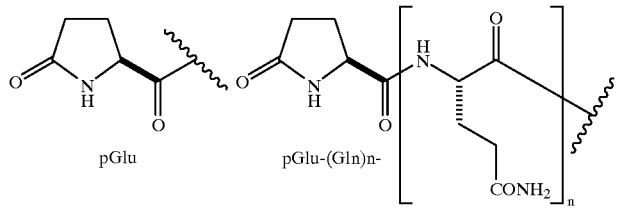
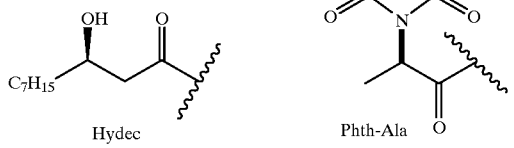

Treatment of 1 with I$_2$/Agl afforded the derivative 14 with iodine ortho to the methoxyl (Scheme 2). Catalytic hydrogenation of 1 (Pd/C, H$_2$) reduced the aromatic ring of MeTyr to give [H$_6$Me$_2$Tyr$_6$]didemnin B (15) and [H$_6$-N-MePhe$^6$] didemnin B (16).

Acyclodidemnin A

Acyclodidemnin A (17), isolated from *T. solidum*, is an acyclic derivative of 2 in which the ester linkage between [Thr$^1$] and [Me$_2$Tyr$^6$] has been hydrolyzed.[20]

Congeners with a Modified Linear Peptide Portion

Acyl Derivatives of DA and DB.

In an earlier study, N-acetyididemnin A (18) was found to be more active than 2 itself, showing cytotoxicity to L1210 cells comparable to that of DB (1).[4a,5] The lipophilicity added to the molecule, and/or endcapping of the N-terminus to neutralize the peptide, presumably increases its cell permeability, resulting in more potent activity.

butyryldidemnin A (20), N$^\alpha$-pentanoyldidemnin A (21), N$^\alpha$hexanoyididemnin A (22), N$^\alpha$-octanoyididemnin A (23), N$^\alpha$-dodecanoyldidenmin A (24), and N$^\alpha$-octadecanoyldidemnin A (25).[2] Didemnin G (=N$^\alpha$formyl DA, 26), an N-formyl derivative of 2, was isolated from *T. solidum*.[4b]

Amino Acid Derivatives

Amino acid derivatives of 2 were also prepared to evaluate the effect of the eighth subunit on activities. Condensation of Z-L-Leu, Z-L-Pro, and Z-D-Pro with 2 followed by catalytic hydrogenation gave N$^\alpha$-L-leucyididemnin A (27),[3a] N$^\alpha$-(L-prolyldidemnin A (28),[3c] and N$^\alpha$-D-prolyididemnin A (29), respectively.

Didemnin B-Type Analogs

Didemnin B-type analogs which have two acyl units after the N-terminus of the didemnin A core were prepared to examine the structural factors contributing to didemnin B's potent bioactivities. The diacyl compounds; acetyl-Pro-OH, propionyl-Pro-OH, isobutyryl-Pro-OH, isobutyryl-D-Pro-OH, O-benzyl-Lac-D-Pro-OH, and O-benzyl-Lac-L-Ala-OH were prepared and condensed with 2 by the mixed anhydride method. Deprotection and purification afforded the corresponding didemnin B-type analogs [acetyl$^9$] didemnin B (31), [propionyl$^9$]didemnin B (32), [isobutyryl$^9$] didemnin B (33), [isobutyryl$^9$-D-Pro$^8$]didemnin B (34), [Ala$^8$]didemnin B (35), and [D-Pro$^8$]didemnin B (36).

Glutaminyl-didemnins

O-pGlu-didemnin B (37) was prepared to evaluate the effect of the number of glutaminyl groups on the bioactivities. Didemnins M (38),[20,25] E (39), and D (40),[4a,7] which are naturally occurring, have O-[pGlu-(glutaminyl)$_n$]-peptide chains (n=1–3) acylating the hydroxyl group of the Lac unit of 1. Didemnins X (41) and Y (42), also isolated from *T. solidum*, have an (R)-3-hydroxydecanoyl terminus after the oligo-Gln peptide chains.[7,20]

Immunomodulating Activity

Two Way Mixed Lymphocyte Response (MLR) Assay

The MLR is a cell-mediated immune response induced by co-culturing two sources of murine splenocytes. In the present case the overall immunomodulatory properties of the didemnins and didemnin analogues were evaluated using a bidirectional MLR derived from murine splenocytes of genetically dissimilar strains of mice. Table I summarizes the biological activities of 42 didemnins in suppressing an immune response in this in vitro assay system.

The results show that all of the didemnin compounds tested suppress the immune response with an IC$_{50}$ value of 0.76 pM (1.0 pg/mL). Other pyroglutamyl didemnins-O-pGlu-DB (37) and didemnin E (39) are the second and third most active (IC$_{50}$ 5.3 and 8.4 pM, respectively). In fact, all four of the pyroglutamyl compounds (37–40) show strong suppression of the MLR. Although the Nα acyl-DA class of nine compounds was distributed over the entire range of potencies, two of the short-chain member, Nα Ac-DA (18) to Nα-hexanoyl-DA (22), were particularly effective, with IC$_{50}$'s of 0.027 nM (0.027 ng/mL) and 0.021 nM (0.022 ng/mL); respectively, for 18 and 22 and Nα-propionyl-butyryl-and pentanoyl-DA's were all in the top half. Short-chain [acyl$^9$] analogues of DB were also quite active.

The native compounds didemnins A and B were in the middle ranking of all compounds tested, whereas most site-modified classifications (chiefly Ist$^2$, Hip$^3$) and long-chain acyl derivatives of DA were in the lower third, containing less potent compounds, with Nα octadecanoyl-DA (25) having the largest IC$_{50}$ at 5110 nM (6040 ng/mL).

Lymphocyte Viability (LcV) Assay

Forty two (42) didemnin compounds (see Table 1) were evaluated for cytotoxicity to one of the lymphocyte populations in the MLR (i.e., Balb/c splenocytes). The purpose of the lymphocyte viability assay (LcV) is to measure metabolic activity in lymphocytes after they have been exposed to the compounds for the duration of an under conditions equivalent to the MLR. The inverse of the data yields cytotoxicity information about the compounds on murine lymphocytes. The rationale of using resting cells, in this case unstimulated lymphocytes, to measure cytotoxicity has a strategic importance. In the MLR the heterogenous cell populations are predominantly resting cells when the assay begins. Transformation (i.e., induction) is initiated upon costimulation by differing lymphocyte populations, but cellular proliferation (i.e., lymphoblast, cells in mitosis) occurs between days 2 and 4 in the murine MLR.[33] Therefore, the first-stage cytotoxic effects of compounds in the assay are most likely to occur early, before lymphoblast develop.

The results show that cytotoxicity of the compounds to lymphocytes occurs over a narrower range of concentrations (3 logs vs 7 logs) as well at much lower potencies (0.074–11.0 μM) than their immune inhibitory effects, thus creating a large therapeutic index, in most cases. For unexplained reasons, the greatest cytotoxicity was observed for [H$_6$Me$_2$Tyr$^G$]DB (15) and Nα-butyryl-DA (20) with LC$_{50}$ values of 0/074 μM) (0.8 μg/mL) and 0.099 μM (0. 10 μg/mL), respectively. The remaining compounds have much lower cytotoxicities.

Lymphocyte Noncytotoxic Immunosuppression

A ratio of cytotoxicity-to-inhibitory effects of the didemnins and their analogues (i.e., a therapeutic index) is also shown in Table 2. This index identifies those compounds which may inhibit an in vitro cell-mediated immune response by noncytotoxic means.

TABLE 5

In Vitro Immunosuppressive Activities of Didemnins[a]

| cmpd # | cmpd name | two-way mixed lymphocyte reaction (MLR) suppression MLR, IC$_{50}$ | | cytoxicity to lymphocytes LcV,$^b$LC$_{50}$ | | ratio LcV (LC$_{50}$)/ MLR (IC$_{50}$) | cytotoxicity to lymphocytes LbV,$^c$LC$_{50}$ μM | ratio LbV (LC$_{50}$)/ MLR (IC$_{50}$) |
|---|---|---|---|---|---|---|---|---|
| | | nM | (ng/mL) | μM | (μg/mL) | | | |
| 38 | Didemnin M | 0.00076 | (0.001) | >7.41 | (>10) | >10,000,000 | 2.5E-4 | 326 |
| 37 | O-pGlu DB | 0.0053 | (0.007) | >8.20 | (>10) | >1,500,000 | 7.9E-5 | 15 |
| 39 | Didemnin E | 0.0084 | (0.012) | >6.77 | (>10) | >800,000 | 1.4E-3 | 169 |
| 22 | N$^α$-hexanoyl DA | 0.021 | (0.022) | 9.60 | (>10) | >460,000 | 1.1E-4 | 5 |
| 18 | N$^α$-acetyl DA | 0.027 | (0.027) | >10.0 | (>10) | >370,000 | 3.9E-4 | 14 |
| 33 | [Isobutyryl$^9$]DB | 0.037 | (0.041) | 2.24 | (2.40) | 60,000 | 2.04E-4 | 6 |
| 40 | Didemnin D | 0.12 | (0.20) | >6.22 | (>10) | >50,000 | 8.5E-4 | 7 |
| 31 | [Acetyl$^9$]DB | 0.21 | (0.22) | 2.80 | (3.10) | 14,000 | 1.6E-4 | 1 |
| 32 | [Propionyl$^9$]DB | 0.23 | (0.26) | 1.98 | (2.20) | 8,500 | 1.84E-4 | 1 |
| 9 | [Anhydro1st$^2$][Phth-Ala$^9$]DB | 0.25 | (0.30) | >8.2 | (>10)) | 33,000 | 1.9E-3 | 7 |
| 5 | Z-[3S,4R,5R-1st$^2$]DA | 0.28 | (0.30) | >9.3 | (>10) | 33,000 | 1.2E-2 | 43 |
| 20 | N$^α$-butyryl DA | 0.30 | (0.30) | 0.099 | (0.1) | 300 | 7.4E-5 | <1 |
| 35 | [Ala$^8$]DB | 0.31 | (0.33) | >9.20 | (>10) | >30,000 | 7.17E-4 | 2 |
| 19 | N$^α$-propionyl DA | 0.37 | (0.37) | 6.50 | (6.50) | 18.000 | 6.8E-5 | <1 |
| 30 | [Pyruvyl$^9$DB (DDB) | 0.38 | (0.43) | 2.60 | (2.90) | 6,800 | 7.9E-5 | <1 |
| 8 | [Phth-Ala$^9$]DB | 0.39 | (0.49) | >8.1 | (>10) | 21,000 | 8.1E-4 | 2 |

TABLE 5-continued

In Vitro Immunosuppressive Activities of Didemnins[a]

| cmpd # | cmpd name | two-way mixed lymphocyte reaction (MLR) suppression MLR, $IC_{50}$ | | cytoxicity to lymphocytes LcV,[b]$LC_{50}$ | | ratio LcV ($LC_{50}$)/ MLR ($IC_{50}$) | cytotoxicity to lymphocytes LbV,[c]$LC_{50}$ | ratio LbV ($LC_{50}$)/ MLR ($IC_{50}$) |
|---|---|---|---|---|---|---|---|---|
| | | nM | (ng/mL) | μM | (μg/mL) | | μM | |
| 1 | DB | 0.42 | (0.46) | 6.34 | (7.00) | 15,000 | 6.0E-4 | 1 |
| 21 | $N^\alpha$-pentanoyl DA | 0.48 | (0.48) | 9.70 | (>10) | 20,000 | 5.9E-5 | <1 |
| 41 | Didemnin X | 0.50 | (0.83) | 6.01 | (10.0) | >2,000 | 3.1E-3 | 6 |
| 42 | Didemnin Y | 0.50 | (0.89) | >5.57 | (>10) | >11,000 | 1.1E-3 | 2 |
| 16 | [$H_6$-NMePhe$^6$] | 0.52 | (0.57) | >9.20 | (>10) | >18,000 | 7.3E-4 | 1 |
| 17 | acyclodidemnin A | 0.57 | (0.54) | >10.4 | (>10) | >18,000 | 0.24 | 436 |
| 34 | [Isobutyryl$^9$-D-Pro$^8$]DB | 0.60 | (0.67) | 5.60 | (6.20) | 9,000 | 4.81E-3 | 8 |
| 14 | [IodoMe$_2$Tyr$^6$]DB | 0.66 | (0.81) | >8.10 | (>10) | >12,000 | 8.2E-4 | 1 |
| 15 | [$H_6$-Me$_2$Tyr$^6$]DB | 0.72 | (0.81) | 0.074 | (0.080) | 100 | 1.6E-3 | 2 |
| 26 | $N^\alpha$-fomyl DA | 0.72 | (0.70) | >10.0 | (>10) | >14,000 | 1.1E-3 | 2 |
| 27 | $N^\alpha$-leucyl DA | 0.74 | (0.78) | >9.50 | (>10) | >13,000 | 3.8E-3 | 5 |
| 36 | [D-Pro$^8$]DB | 0.83 | (0.92) | >9.00 | (>10) | 11,000 | 0.013 | 15 |
| 11 | [oximHip$^3$]DB | 0.85 | (0.96) | >8.9 | (>10) | 10,000 | 1.7E-3 | 2 |
| 28 | $N^\alpha$-prolyl DA | 0.96 | (1.00) | >9.60 | (>10) | >10,000 | 5.1E-3 | 5 |
| 2 | DA | 0.98 | (0.93) | >11.0 | (>10)[d] | 11,000 | 0.015 | 15 |
| 3 | Z-DA | 1.02 | (1.10) | 7.50 | (8.10) | 7400 | 1.9E-3 | 2 |
| 23 | $N^\alpha$-octanoyl DA | 5.10 | (5.50) | >9.35 | (>10) | 1,800 | 0.021 | 4 |
| 29 | $N^\alpha$-D-prolyl DA | 11.7 | (12.2) | >9.60 | (>10) | >8,000 | 0.022 | 2 |
| 4 | Z-[3R,4R,5S-1st$^2$]DA | 18.0 | (19.0) | 9.00 | (9.70) | 500 | 0.22 | 12 |
| 10 | [$H_2$-Hip$^3$]DA | 30.5 | (29.0) | >10.6 | (>10) | 350 | 0.46 | 16 |
| 13 | didemnin N | 34.2 | (37.0) | >9.20 | (>10) | >270 | 2.1E-1 | 1 |
| 12 | [epiHip$^3$]DA | 86.0 | (81.0) | >10.6 | (>10) | 120 | 5.1E-2 | 1 |
| 7 | O-acetyl DA | 100 | (100) | >10.0 | (>10) | 100 | 7.7E-2 | 1 |
| 24 | $N^\alpha$-dodecanoyl DA | 106 | (119) | >8.90 | (>10) | >84 | 0.16 | 2 |
| 6 | Z-[3S,4S,5S-1st$^2$]DA | 270 | (290) | >9.3 | (>10) | 34 | 2.6 | 9 |
| 25 | $N^\alpha$-octadecanoyl DA | 5110 | (6040) | >8.50 | (>10) | >2 | 2.7 | 1 |

[a]Arranged in order of IC50's (most active to least active) in MLR.
[b]LcV = Lymphocyte viability.
[c]LbV = Lymphoblast viability.
[d]Highest concentration 10 μg/mL.

Five compounds showed very large ratios (more than 10$^5$). These are the most active compounds (in the same order) in the mixed lymphocyte reaction, the pyroglutamyl-substituted didemnins B and the short-chain acyl-substituted didemnins A. Similarly, at the bottom of the list is Nα-octadecanoyldidemnin A (25), with a ratio of 2, which correlates well with its lowest ranking in the MLR ($IC_{50}$ 5.110 nM) and moderate cytotoxicity (>8.50 μM). O-pGLu-DB (37) is the only synthetic analogue of didemnin B represented in this group, with a noncytotoxic inhibition ration of 1,500,000.

The parent compounds didemnins A and B, showed similar midrange ratios between 10,000 and 15,000, with site-modified analogues of each distributed about equally above and below each parent compound.

Lymphoblast Viability (LbV) Assay

The didemnins were also evaluated for cytotoxicity to a blastogenic from of the lymphocytes. Concanavalin A, the T-cell mitogen, was used to induce cellular proliferation of the splenocytes. Since cellular proliferation occurs between days 2 and 4 in the murine MLR, there may be secondary cytotoxic effects of the compounds occurring later as lymphoblast develop. This form of the cell is more fragile and therefore usually more susceptible to cytotoxicity.

The results show that the cytotoxicity of the compounds to lymphoblast occurs over a much wider range of concentrations than was observed toward lymphocytes (see, Table 2). Not unexpectedly, much lower cytotoxic concentrations (down to 7.9E-5 μM) were generally observed compared to lymphocytes.

The order of cytotoxicity to lymphoblast is generally, but not exactly, like that seen for cytotoxicity to lymphocytes. One exception seems to be for O-pGlu-DB (37), which ranked higher in cytotoxicity to lymphoblast than to lymphocytes. This change in rank accounts for a marked difference in the ratios of noncytotoxic immunosuppression discussed below.

Lymphoblast Noncytotoxic Immunosuppression

Some important differences between lymphocyte and lymphoblast assays are observed. First, the toxicity/suppression ratios are smaller in the lymphoblast assay, indicating that the inhibition of the immune response at later stages in the reaction would be most affected by cytotoxicity to proliferating immune cells. However, the exception to this consistent with a judgment of noncytotoxic immunosuppression, occurs for AcycloDA (17), didemnin M (38), and didemnin E (39). The ratios are larger as a group to distinguish them as compounds that might rely on other means to inhibit the immune reaction than via cytotoxicity involving lymphoblast. Didemnins M and E have this distinction whether the cytotoxicity data are for lymphocytes or lymphoblasts.

Graft vs Host Reaction (GVHR)

Three representative compounds didemnin M (38), O-pGlu-DB (37), and didemnin B (1)-showing high (37,38) or moderate (1) in vivo immunosuppressive activity were subsequently evaluated in a multidose assay (0.16,0.016, and 0.0016 mg/kg per injection; qd 1–7) for their in vivo immunosuppressive effects on the GVHR splenomegaly assay. These data are shown below in Table 3:

TABLE 6

Immunosuppression of Didemnins on Graft-vs.-Host Reaction (GVHR) Assay[a]

| compound | dose[b] (mg/Kg/day) | body weight[c] day 0 (g ± SD) | body weight day 5 (g ± SD) | body weight change day 5 (g) | alive day 8 (%) | mean group spleen wt. normalized to day 8 body weight | index[d] |
|---|---|---|---|---|---|---|---|
| Didemnin B (1) | 0.16 | 17.0 ± 0.9 | 15.6 ± 1.6 | −1.4 | 100 | 4.0 | 1.24 |
|  | 0.016 | 17.2 ± 0.7 | 18.2 ± 0.7 | 1.0 | 100 | 4.2 | 1.33 |
|  | 0.0016 | 17.4 ± 0.8 | 18.4 ± 0.8 | 1.0 | 100 | 6.1 | 1.91 |
| Didemnin M (38) | 0.16 | 16.6 ± 0.8 | 16.4 ± 1.0 | 1.0 | 100 | 4.9 | 1.54 |
|  | 0.016 | 16.6 ± 0.5 | 17.8 ± 0.7 | −0.2 | 100 | 4.4 | 1.38 |
|  | 0.0016 | 15.8 ± 1.3 | 17.2 ± 1.2 | 1.4 | 100 | 4.1 | 1.27 |
| Q-pGlu DB (37) | 0.16 | 15.8 ± 1.2 | 15.2 ± 1.2 | −0.6 | 100 | 4.2 | 1.32 |
|  | 0.016 | 16.4 ± 0.8 | 17.2 ± 1.5 | 0.8 | 100 | 5.6 | 1.76 |
|  | 0.0016 | 17.0 ± 1.5 | 17.4 ± 1.7 | 0.4 | 100 | 5.2 | 1.63 |
| Positive Control[e] |  | 16.8 ± 1.0 | 18.0 ± 1.3 | 1.2 | 100 | 5.4 | 1.70 |
| Syngenetic[f] |  | 16.6 ± 0.5 | 18.0 ± 1.3 | 1.4 | 100 | 3.2 | 1.00 |
| Cyclophosphamide | 200 | 16.3 ± 0.4 | 13.8 ± 0.4 | −2.5 | 100 | 0.4 | 0.14 |

[a]Balb/c-to-CB6Ft GVHR model. See Experimental Section for detail.
[b]Schedule QD 1–7, 0.5 mL solution/mouse.
[c]Mice were weighted days 0, 5, 8.
[d]Index = Spleen wt. treated/spleen wt. syngenetic injection. >1.3 (50% suppression of positive control is considered to by significant suppression).
[e]Vehicle only.
[f]Syngenetic (CB6F6-CB6F1) injection.

The results show didemnin M (38) optimally suppressed the allogeneically induced splenomegaly response in CB6F1 mice grafted with Balb/c splenocytes at 1.6 μg/kg/inj by 61% compared to control (see, Table 3). Higher doses (16 and 160 μg/kg) were less effective, but not toxic. Didemnin B (2) and O-pGlu-DB (37) were equally effective but at optimal dosages of 160 μg/kg per injection, showing 66% and 54% suppression, respectively. These were the highest doses for each and neither was toxic to the animals. Lower doses were less effective for O-pGlu-DB. Didemnin B showed a 53% suppression at the next lower dose of 16 μg/kg per injection but was not effective at the lowest dose (1.6 μg/kg per injection)). The relationship of these in vivo effects correlates well with their in vitro data.

The immunology data suggest that the immunosuppressive activity of didemnins is mediated mostly by cytotoxicity to lymphoblast occurring at a later stage of activation in the cell-mediated immune response, except for some glutaminyl didemnins, 37–39, and acyclo-DA (17), as indicated by the relatively constant therapeutic index utilizing cytotoxicity data to proliferating lymphoblast versus resting lymphocytes. These results indicate that the immunosuppressive activity of didemnins is, in most cases, a result of antiproliferation of stimulated T-cells, as demonstrated for 1 by others.[36] In the cases of 37–39 and 17, however, some unique or specific mechanisms of action such as those seen in cyclosporin A[37], FK 506, or rapamycin[38] may be involved in the immunosuppressive action (e.g., noncytotoxic immunosuppression during early stage events involving T-cell activation).

Administration Regimes

"Unit dose" as it pertains to the delivery of the didemnin compounds refers to physically discrete units suitable as unitary dosages for animals, each unit containing a predetermined quantity of active didemnin material calculated to produce the desired immunogenic effect in association with the required diluent; i.e., carrier, or vehicle. The specifications for each unit dose are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Unit dosage forms are typically prepared from the frozen or dried antibody by dispersement in a physiologically tolerable (acceptable) diluent or vehicle such as water, saline or phosphate-buffered saline to form an aqueous composition. Such diluents are well known in the art and are discussed, for example, in Remington's Pharmaceutical Sciences, 16th Ed., Mack Publishing Company, Easton, Pa. (1980) at pages 1465–1467.

Dosage forms can also include an adjuvant as part of the diluent.

Adjuvants such as Complete Freund's Adjuvant (CFA), Incomplete Freund's Adjuvant (IFA) and alum are materials well known in the art, and are available commercially from several sources.

The dosage of such compounds will be dependent upon the immunomodulatory response desired, the type of host involved, its age, health, weight, kind of concurrent treatment (if any) frequency of treatment, therapeutic ratio and like considerations. Typical dosage levels of the immunomodulatory didemnin compounds can be for example: i.v., 0.01 to about 20 mg/kg; i.p., 0.01 to about 100 mg/kg; s.c., 0.01 to about 100 mg/kg; i.m., 0.01 to about 100 mg/kg; topical, 1 to about 500 mg/kg; oral, 0.01 to about 200 mg/kg; and intranasal, 0.01 to about 100 mg/kg of total body weight.

EXAMPLES

The present invention will be further illustrated with reference to the following examples which aid in the understanding of the present invention, but which are not to be construed as limitations thereof. All percentages reported herein, unless otherwise specified, are percent by weight. Optical rotations were measured using a 5-cm cell (1 mL). NMR spectra (200, 300 and 500 MHz, $^1$H) were obtained using either deuterochloroform ($CDCl_3$), deuteromethanol ($CD_3OD$) or a mixture of both as solvents and internal standard [7.26 ($^1$H) and 77.0 ($^{13}$C)ppm for $CDCl_3$ 3, 3.30 ($^1$H) and 49.0 ($^{13}$C) ppm for $CD_3OD$ or a mixture of $CD_3OD$-$CDCl_3$]. FABMS spectra and HRFABMS data were obtained using magic bullet as a matrix. All solvents for reactions were distilled over appropriate drying agents prior to use. RP-HPLC was performed by using a semi-preparative C-18 silica gel column with UV detection at 254 nm and a flow rate of 1 mL/min. Solvent systems are indicated in each case.

Preparation of Didemnin Congeners

Native Didemnins. All native didemnins were isolated from the extract of *Trididemnum solidum* except for dehydrodidemnin B (30), which was isolated from *Aplidium albicans*[21] Isolation and structure determination of these peptides have been described elsewhere.[3,20,21]

Boc(3R,4R,5S)-Ist-OH. Boc(3R,4R,5S)-Ist-OEt[22] (130 mg, 0.43 mmol) was treated with KOH (1N, 0.5 mL) in dioxane (1.0 mL) and $H_2O$ (0.5 mL) at rt for 1 hr. An oily product (98 mg, 83%) was afforded after the usual work-up: $[\alpha]_D^{25}$+33° (c 0.13, $CHCl_3$); $^1H$ NMR (200 MHz, $CDCl_3$) δ 4.88 (1H, d, J=10.0 Hz), 4.22 (1H, m), 3.32 (1H, m), 2.6–2.5 (2H, m), 1.45 (9H,s). HRFABMS: calcd for $C^{13}H_{26}NO_5$, Mr 276.1811 (M+H); found, 276.1816.

Boc('3S,4R,5R)-Ist-OH. Boc(3S,4R,5R)-Ist-OEt122 was treated as above to give an oil (84%): $[\alpha]_D^{25}$–1.2° (c 0.27, $CHCl_3$); $^1H$ NMR (200 MHz, $CDCl_3$) $^1H$ NMR (200 MHz, $CDCl_3$) δ 4.50 (1H, d, J=9.8 Hz), 4.06 (1 H, m), 3.60 (1H, m), 2.6–2.4 (2H, m), 1.45 (9H, s). HRFABMS: found, 276.1804.

Boc(3S,4S,5S)-Ist-OH. Boc(3S,4S,5S)-Ist-OEt was treated as above to give an oil (84%): $[\alpha]_D^{25}$–41.3° (c 0.29, $CHCl_3$); $^1H$ NMR22 (200 MHz, $CDCl_3$) δ 64.90 (1H, d, J=10.0 HZ), 4.27 (1H, m), 3.22 (1H, m), 2.7–2.4 (2H, m), 1.45 (9H, s). HRFABMS: found, 276.1804.

Boc(3R,4R,5S)-Ist(TBDMS)-OH. Boc(3R,4R,5S)-Ist-OH (97 mg, 0.35 mmol) was treated with t-butyldimethylsilyl (TBDMS) chloride (0.16 g, 0.45 mmol) in the presence of imidazole (145 mg, 2.1 mmol) in DMF (1.1 mL) under $N_2$ for 20 hrs. The product was chromatographed ($SiO_2$, hexane-EtOAc, 1:4) to give an oil (80 mg, 59%). $[\alpha]_D^{25}$ +21° (c 0.29, $CHCl_3$): $^1H$ NMR (200 MHz, $CDCl_3$) δ 4.72 (1H, d, J=9.0 Hz), 4.33 (1H, m), 3.37 (1H, m), 2.7–2.4 (2H, m), 1.46 (9H, s), 0.90 (9H, s), 0.09 and 0.07 (6H, 2:1 singlets). HRFABMS:

calcd for $C_{19}H_{40}NO_5Si$, Mr 390.2676 (M+H); found, 390.2662.

Boc(3S,4R,5R)-Ist(TBDMS)-OH. The above treatment of Boc(3S,4R,5R)-Ist-OH gave an oil (63%): $[\alpha]_D^{25}$–0.740 (c 0.41, $CHCl_3$); 1 H NMR (200 MHz, $CDCl_3$) δ 6.64 and 4.50 (0.5 H each, d, J=9.0 Hz), 4.17 (1H, m), 3.70 and 3.30 (0.5H each, m), 2.6–2.4 (2H, m), 1.46 and 1.43 (9H, s), 0.88 (9H, brs), 0.11 and 0.02 (6H, 4:1 singlets).

HRFABMS: found, 390.2680.

Boc(3S,4S,5S)-Ist(TBDMS)-OH. The above treatment of Boc(3S,4S,5S -1st-OH gave an oil (58%); $[\alpha]_D^{25}$–30.3° (c 0.37, $CHCl_3$). $^1H$ NMR (200 MHz, $CDCl_3$) δ 4.75 (1H, d, J=9.0 Hz), 4.37 (1H, m), 3.30 (1H, m), 2.6–2.4 (2H, m), 1.46 (9H, s), 0.90 (9H, brs), 0.12 (6H, s). HRFABMS: found, 390.2676.

Boc(3-R,4R,5S)-Ist(TBDMS)-Hip-Leu-OTMSE. A solution of DCC (1,3-dicyclohexylcarbodiimide, 44 mg, 0.22 mmol) in $CH_2Cl_2$ (1 mL) was added to a stirred solution of Hip-Leu-OTMSE[23] (74 mg, 0.19 mmol), Boc(3R,4R,5S)-Ist(TBDMS)-OH (74 mg, 0.19 mmol) and DMAP (N,N-dimethylaminopyridine, 23 mg, 0.19 mmol) in $CH_2Cl_2$ (3 mL) at 0° C. The reaction mixture was stirred at 0° C. for 1 hr then at rt for 12 h. The product was chromatographed ($SiO_2$, EtOAc-hexane 9:1) to give a viscous oil (54 mg, 37%): $[\alpha]_D^{25}$–7.50 (c 0.28, $CHCl_3$). HRFABMS: calcd for $C_{30}H_{75}N_2O_9Si$, Mr 759.5011 (M+H); found, 759.5035.

Boc(3S,4R,5R)-Ist(TBDMS)-Hip-Leu-OTMSE. (51%): $[\alpha]_D^{25}$–19° (c 0.34, $CHCl_3$). HRFABMS: found, 759.4998.

Boc(3S,4S,5S)-Ist(TBDMS)-Hip-Leu-OTMSE. (40%): $[\alpha]_D^{25}$–27° (c 0.33, $CHCl_3$). HRFABMS: found, 759.501 1.

Boc(3S,4S,5S)-Ist-Hip-Leu-OH. A solution of Boc(3R,4R,5S)-Ist(TBDMS)-Hip-Leu-OTMSE (65 mg, 0.086 mmol) in THF (0.6 mL) was stirred with tetrabutylammonium fluoride (TBAF) solution (1 M, 0.195 μL in THF) at rt for 3 days. Water was added to the product after removal of the organic solvent. Crude oily material was obtained after the usual work-up which was separated ($SiO_2$, $CHCl_3$–MeOH 9:1) to give an oil (45 mg, 96%): $[\alpha]_D^{24}$ –9.8° (c 0.31, $CHCl_3$). HRFABMS: calcd for $C_{27}H_{49}N_2O_9$, Mr 545.3438 (M+H); found, 545.3444.

Boc(3S,4R,5R)-Ist-Hip-Leu-OH. (87%): $[\alpha]_D^{24}$ –11° (c 0.25, $CHCl_3$). HRFABMS: found, 545.3444.

Boc(3S,4S,5S)-Ist-Hip-Leu-OH. (88%): $[\alpha]_D^{24}$ –21° (c 0.25, $CHCl_3$). HRFABMS: found, 545.3432.

Z-D-MeLeu-Thr-{O-[Boc-(3R,4R 5S)Ist-O-Hip-Leu-Pro-$Me_2$Tyr]}-OTMSe. A solution of Boc(3S,4R,5R)-Ist-Hip-Leu-OH (30 mg, 0.055 mmol) and N-hydroxybenzotriazole (HOBT, 13.5 mg, 0.1 mmol) in THF (0.4 mL) was added to a solution of Z-D-MeLeu-Thr-[O-(Pro-$Me_2$Tyr)]-OH.HCl (40 mg, 0.050 mmol) in DMF (0.3 mL) in the presence of N-methylmorpholine (NMM, 4 μL). A solution of EDC [1-(3-dimethyl-amino-propyl)-3-ethylcarbodiimide hydrochloride, 11.5 mg, 0.056 mmol] in THF (0.3 mL) was added at 0° C. The reaction mixture was stirred at 0° C. for Ih then at rt for 12 h. The products were purified by RP-HPLC (MeOH-$H_2O$, 9:1). Two products (epimers at the (x-position of Hip, identical FABMS data) were combined (yield 41.5 mg, 58%): $[\alpha]_D^{25}$–0.90 (c 0.89, $CHCl_3$). HRFABMS: calcd for $C_{67}H_{107}N_6O_{17}Si$, Mr 1295.7462 (M+H); found, 1295.7460.

Z-D-MeLeu-Thr-{O-[Boc-(3S,4R,5R)Ist-O-Hip-Leu-Pro-$Me_2$Tyr]}-OTMSe. (50%): $[\alpha]_D^{25}$ –9° (c 0.89, $CHCl_3$). HRFABMS: calcd for $C_{67}H_{107}N_6O_{17}Si$, Mr 1295.7462 (M+H); found, 1295.7471.

Z-D-MeLeu-Thr-{O-[Boc-(3S,4S,5S)Ist-O-Hip-Leu-Pro-$Me_2$Tyr]}-OTMSe. (50%): $[\alpha]_D^{25}$ –9° (c 0.19, $CHCl_3$). HRFABMS: calcd for $C_{67}H_{107}N_6O_{17}Si$, Mr 1295.7462 (M+H); found, 1295.7460.

Z-[(3R,4R,5S)Ist$^2$]Didemnin A (4). A stirred solution of Z-D-MeLeu-Thr-{O-[Boc-(3R,4R,5S)Ist-O-Hip-Leu-Pro-$Me_2$Tyr]}-OTMSE (40 mg, 0.031 mmol) in THF (0.2 mL) was treated with tetrabutyl- ammonium fluoride (1 M in THF, 0.12 mL) for 16h. A viscous oil (35 mg, FABMS m/z 1195) was obtained after the usual work-up which showed one spot on TLC ($SiO_2$). To this product (in $CH_2Cl_2$, 0.2 mL) TFA (0.25 mL) was added at 0° C. The reaction mixture was stirred at 0° C. for I h. Excess TFA was removed in vacuo to give the ninhydrin-positive product (36 mg, m/z 1096 by FABMS, TLC one spot). NMM (4 μL) was added to a solution ($CH_2Cl_2$, 1 mL) of the above product at 0° C., followed by $CH_2Cl_2$ (15 mL). To a stirred solution of HOBT (14.1 mg, 0.10 mmol) and EDC (14.2 mg, 0.070 mmol) in DMF (0.5 mL) and $CH_2Cl_2$ (60 mL) the above mixture was added slowly over 6 h at 0° C. The reaction mixture was stirred at rt for four days, then concentrated. The EtOAc soluble portion was washed, and the product (27 mg) was separated by RP-HPLC (MeOH—$H_2O$85:15) to give a solid (2.3 mg, 6%). This product, a mixture of Z-didemnin A and its epimer at the (α-position of the Hip residue, was separated by HPLC (silica gel, EtOAc-hexane 3:2). The first fraction and the second fraction gave Z-[(3R,4R,5S)Ist$^2$,]didemnin A, (4) and Z-[(3R,4R,5S)Ist$^2$, α-epi-Hip$^3$] didemnin A, respectively.[23] Compound 4: colorless solid $[\alpha]_D^{25}$–14° (c 0.16, $CHCl_3$). HRFABMS: calcd for $C_{57}H_{85}N_6O_{14}$, Mr 1077.6124 (M+H); found, 1077.6115.

Z-[(3S,4R,5R)-Ist$^2$]Didemnin A (5). Yield 19%, colorless solid, $[\alpha]_D^{25}$ –102° (c 0.11, CHCl$_3$). HRFABMS: found, 1077.6124.

Z-[(3S,4S,5S)-Ist$^2$]Didemnin A (6). Yield 14%, colorless solid, $[\alpha]_D^{25}$ –28° (c 0.11, CHCl$_3$). HRFABMS: found, 1077.6124.

O-Acetyldidemnin A (7). To a solution of 2 (55.2 mg, 0.059 mmol) in benzene (0.8 mL) was added benzyl chloroformate (50 mL, 6 eq) and Et$_3$N (10 μL). The mixture was stirred at rt for 24 h then the solvents were removed by N$_2$. The resulting solid was separated (silica gel, EtOAc), to give N-Z-didemnin A. The product was treated with pyridine (0.5 mL) and acetic anhydride (0.5 mL) for 12 h at rt to give N-Z-O-acetyldidemnin A (63 mg, 92%); $^1$H NMR (CDCl$_3$, 300 MHz).$^1$ HRFABMS: calcd for C$_{59}$H$_{87}$N$_6$O$_{15}$, M$_r$ 111 9.6229 (M+H); found, 1119.6217.

A mixture of N-Z-O-acetyldidemnin A (40 mg 0.035 mol) and Pt/C (10%, 40 mg) in 2-propanol (1 mL) and acetic acid (10 mL) was stirred in a H$_2$ atmosphere for 2.5 h at rt. The product was filtered through a short (4 g) silica gel column with EtOAc-2-propanol (4:1). The residue was purified by HPLC (silica gel, EtOAc) to give 7 (6 mg, 17%); $[\alpha]_D^{24}$ –136° (c 0.38, CHCl$_3$): white powder; IR (film) 3319, 1734, 1653, 1635 cm$^{-1}$; $^1$H NMR (300 MHz).$^1$ FABMS m/z 986 (M+H). HRFABMS: calcd for C$_{51}$H$_{81}$N$_6$O$_{13}$, m/z 985.5861 (M+H); found, 985.5871.

[(2S,3R,4S)-H$_2$Hip$^3$]Didemnin A (10). A solution of NaBH$_4$ (3.50 mg, 0.095 mmol) in THF—H$_2$O (1:1,2 mL) was added dropwise to a solution of 2 (79.4 mg, 0.084 mmol) in THF (2 mL) at 0° C. The mixture was stirred at 0° C. for 50 min and the temperature was elevated to rt over 2 h; HCl (1 N, 90 μL) was added, and the product was extracted with CH$_2$Cl$_2$. The organic layer was concentrated to give a solid (79.2 mg) which was chromatographed (silica gel, CHCl$_3$—MeOH, 6:1) to give nearly pure 10 (53.4 mg, 67%). A portion was purified by RP-HPLC (MeOH—NaCl 0.4M, 7:1): HRFABMS: calcd for C$_{49}$H$_{81}$N$_6$O$_{12}$, M$_r$ 945.5912 (M+H); found, 945.5934.

[Hip$^3$oxime]Didemnin B (11). To a solution of 1 (25.1 mg, 22.6 mmol) in CH$_3$OH (1 mL) was added NH$_2$OH—HCl (57.3 mg, 825 mmol) followed by (C$_2$H$_5$)$_3$N (115 mL, 825 mmol). The solution was stirred at rt for 1 week and concentrated (N$_2$). The residue was chromatographed as above, to give 11 (11.9 mg, 47%): $^1$H NMR (CDCl$_3$, 500 MHz)$^1$ δ 7.70 (1H, d, J 9.7), 7.67 (1H, d, J=5.2), 7.40 (1H, d, J=10.0), 6.09 (1H, d, J=5.4 Hz, Hip-α). HRFABMS: calcd for C$_{57}$H$_{91}$N$_8$O$_{15}$, M$_r$ 1127.6604 (M+H); found, 1127.6619.

Iodididemnin B (14). To a solution of 1 (5.5 mg, 0.005 mmol in CH$_2$Cl$_2$ 0.2 mL) was added CF$_3$CO$_2$Ag (8.8 mg, 0.04 mmol) followed, dropwise, by a solution Of I$_2$ (10 mg, 0.04 mmol in CH$_2$Cl$_2$, 0.2 mL). The suspension was stirred overnight at rt. Excess reagents were removed (filtration, Na$_2$SO$_3$ wash). The solvent was removed and the crude product was purified by HPLC (C-18, MeOH—H$_2$O,7:1) to give 14 (5.0 mg, 82%): $^1$H NMR (CDCl$_3$) $^1$H NMR δ 7.51 (1H, s), 7.15 (1H, d, J=8.0 Hz), 6.77 (1H, d, J=8.0 Hz), 3.87 (3H, s), 2.59 (3H, s, N—CH$_3$). HRFABMS: calcd for C$_{57}$H$_{89}$IN$_7$O$_{15}$, M$_r$ 1238.5461 (M+H); found, 1238.5458.

[H$_6$Me$_2$Tyr$_6$]Didemnin B (15) and [H$_6$-N-MePhe$^6$] Didemnin B (16). A mixture of 1 (16.3 mg, 0.015 mmol), Pt/C (10%, 38.3 mg), and TFA (20 μL) in CH$_3$OH (5 mL) was stirred under H$_2$ for 4 ht rt. The mixture was filtered through a C-18 Sep-pak with MeOH and concentrated to give a solid (33.1 mg), which was separated by HPLC (C-18, CH$_3$OH-0.4 M NaCl, 7:1) to give 15 (3.3 mg, 20%) as a white powder: $[\alpha]_D^{23}$ –29° (c 0.41, CHCl$_3$); $^1$H NMR (CDCl$_3$, 500 MHz).$^1$ HRFABMS: calcd for C$_{57}$H$_{96}$N$_7$O$_{51}$ M$_r$ 1118.6964 (M+H); found, 1118.7001.

Fraction 2 yielded 16 (5.2 mg, 32%) as a white solid: $[\alpha]_D^{24}$ –29° (c 0.41, CHCl$_3$);$^{-1}$H NMR (CDCl$_3$, 500 MHz).$^1$ HRFABMS: calcd for C$_{56}$H$_{94}$N$_7$O$_{14}$, M$_r$ 1088.6859 (M+H); found, 1088.6902.

N$^\alpha$-Acetyldidemnin A (18) was prepared from 2 as described.$^{3c}$ HRFABMS: calcd for C$_{51}$H$_{81}$N$_6$O$_{13}$, M$_r$ 985.5862 (M+H); found, 985.5880.

N$^\alpha$-Propionyldidemnin A (19) was prepared from 2 as described.$^{3c}$ HRFABMS: calcd for C$_{52}$H$_{83}$N$_6$O$_{13}$, M$_r$ 999.6018 (M+H); found, 999.5985.

N$^\alpha$-n-Butyryldidemnin A (20). To a solution of 2 (30 mg, 31 mmol) in dry CH$_2$Cl$_2$ was added n-butyric anhydride (10 mg, 0.63 mmol) at 0° C. followed by a catalytic amount (2 mg) of DMAP. The mixture was left at 0° C. for 48 h. EtOAc and aqueous NaHCO$_3$ were added and the organic layer was dried (Na$_2$SO$_4$), concentrated, and separated to give 20 (27 mg, 86%), colorless solid: HRFABMS: calcd for C$_{53}$H$_{84}$N$_6$O$_{13}$, M$_r$ 101 3.6185 (M+H); found, 1013.6175.

N$^\alpha$-Acyl[Pentanoyl (21), Hexanoyl (22), Octanoyl (23), Dodecanoyl (24), Hexadecanoyl (25)]Didemnins. General method: EDC (0.31 mmol) was added at 10° C. to a stirred solution of the free acid (0.63 mmol) in CH$_2$Cl$_2$ (2 mL). The mixture was allowed to react for 1.5 h at 10° C., 2 (0.31 mmol) was added to the solution, and the reaction mixture was stirred for 2 h at 10° C. then left at –20° C. for 20 h. The mixed anhydride (prepared as above, 0.31 mmol) was added and the reaction mixture was allowed to stand at 0° C. for 24 h. Solvent was evaporated and the product after usual work up was purified (SiO$_2$, CHCl$_3$—MeOH 3–5%) to give the corresponding N$^\alpha$-acyldidemnins.

N$^\alpha$-Pentanoyldidemnin A (21). Yield 90%: HRFABMS: calcd for C54H$_{87}$N$_6$O$_{13}$, M$_r$ 1027.6331 (M+H); found, 1027.6306.

N$^\alpha$-Hexanoyldidemnin A (22). Yield 90%: HRFABMS: calcd for C$_{55}$H$_{89}$N$_6$O$_{13}$, M$_r$ 1041.6488 (M+H); found, 1041.6477.

N$^\alpha$-Octanoyldidemnin A (23). Yield 90%: HRFABMS: calcd for C57H$_{93}$N$_6$O$_{13}$, M$_r$ 1069.6791 (M+H); found, 1069.6785.

N$^\alpha$-Dodecanoyldidemnin A (24). Yield 89%: HRFABMS: calcd for C$_{61}$H$_{101}$N$_6$O$_{13}$, M$_r$ 1125.7427 (M+H); found, 1125.7401.

N$^\alpha$-Octadecanoyldidemnin A (25). Yield 89%. HRFABMS: calcd for C$_{67}$H$_{113}$N$_6$O$_3$, (M+H); found, 1181.8040.

N$^\alpha$-(D-Pro)-Didemnin A (29). DCC (24.4 mg, 0.12 mmol) was added to a solution of Z-D-proline (Pro) (59 mg, 0.24 mmol) in CH$_2$Cl$_2$ (0.5 mL) at 5° C. The mixture was stirred at 5° C. for 2 h. Compound 2 (75.4 mg, 0.08 mmol) in CH$_2$Cl$_2$ (0.5 mL) was added and the mixture was allowed to stand for 8 h at 10° C., then was concentrated. The residue was suspended in cold EtOAc, filtered, and concentrated in vacuo to an oil which was separated (silica gel, EtOAc-CH$_2$Cl$_2$, 7:3), to give N-(Z-D-Pro)didemnin A as a white powder (83.9 mg, 0.071 mmol, 89%): $^1$H NMR (CDCl$_3$, 300 MHz) δ 7.9* ($^1$H, m), 7.2–7.4 (5H, m), 7.05 (2H, d, J=8.4), 6.82 (2H, d, J=8.4), 3.76 (3H, s), 2.88*, 2.89*, 2.77* (s), 2.55*, 2.52* (s) (*peaks were observed as pairs.). HRFABMS: calcd for C$_{62}$H$_{92}$N$_7$O$_{15}$, M$_r$ 1174.6651 (M+H); found, 1174.6663.

A mixture of N-(Z-D-prolyl)didemnin A (80 mg, 0.077 mmol) and Pd/C (10%, 36 mg) in MeOH (2 mL,) was stirred vigorously in a hydrogen atmosphere for 2 h at rt, filtered through a C-18 Sep-pak column with MeOH, and concentrated to a white powder (65.6 mg). A portion (17.0 mg) of the powder was separated by HPLC to give pure 29 (11.9 mg, 57%), white powder; $^1$H NMR (CDCl$_3$, 300 MHz) δ 7.97–7.3 (br NH's) 7.07 (2H, d, J=8–4), 6.83 (2H, d, J=8.4), 3.79 (3H, s), 2.92 (3H, br s), 2.53 (3H, S). HRFABMS: calcd for C$_{54}$H$_{86}$N$_7$O$_{13}$, M$_r$ 1140.6284 (M+H); found, 1140.6285.

N$^α$-(L-Pro)Didemnin A (28).$^{3c}$ Z-L-Pro was coupled to 2 and deprotected as above to give a white powder (27% overall): $^1$H NMR (CDCl$_3$, 300 MHz)$^1$ δ 8.03 (1H, d, J=8.7), 7.73 (1H, br d, J=9.6), 7.33 (1H, br s), 7.06 (2H, d, J=8.4), 6.84 (2H, d, J=8.4), 3.88 (3H, s), 3.02 (3H, s), 2.53 (3H, s). HRFABMS: found, 1040.6277.

N-(L-Leu)Didemnin A (27). A sample of 27 prepared previously$^{3c}$ was re-purified by RP-HPLC (MeOH—NaCl 0.4 M, 7:1).

[Acetyl$^9$]Didemnin B (31). To a suspension of L-Pro (247 mg, 2.15 mmol) in pyridine (1 mL) acetic anhydride (1 mL) was added, and the mixture was stirred at rt for 5 min. The solvent was removed in vacuo and the resulting oil was partitioned between EtOAc and HCl (1 N). The organic layer was dried over Na$_2$SO$_4$, concentrated, and the resulting solid was recrystallized from EtOAc to give N-Ac-L-Pro (167 mg, 44%), a white powder: mp 108° C. [lit 115° C. (from CHCl$_3$)$^{43}$]; [α]$_D^{25}$ –171° (c 0.91, CHCl$_3$). Anal. (C$_7$H$_{11}$NO$_3$) C, H, N.

N-Ac-L-Pro (31 mg, 0.197 mmol) was treated with DCC (20.3 mg, 0.099 mmol) in CH$_2$Cl$_2$ (0.1 mL) for 4 h at 10° C. A solution of 2 (62 mg, 0.068 mmol) in CH$_2$Cl$_2$-DMF (6:4, 1 mL) was added to the mixture at 5° C. The mixture was allowed to stand at 5° C. for 12 h, filtered, and then concentrated in vacuo. The resulting solid was separated (silica gel, EtOAc-2-propanol, 10:1), to give 31 (63 mg, 0.058 mmol, 88%) as a white powder: $^1$H NMR (CDCl$_3$, 500 MHz).$^1$ HRFABMS: calcd for C$_{56}$H$_{88}$N$_7$O$_{14}$, M$_r$ 1082.6389 (M+H); found, 1082.6396.

[Propionyl$^9$]Didemnin B (32). Propionic anhydride (2.60 g, 0.02 mol) was added to a suspension of L-Pro (1.15 g, 0.01 mol) in pyridine (2 mL). The mixture was stirred for 30 min at rt, solvent was removed in vacuo, and the product was recrystallized from EtOAc to give N-propionyl-L-Pro (1.60 g, 96%): colorless needles; mp 98–99° C.; [α]$_D^{25}$ –1860° (c 1.7, CHCl$_3$); $^1$H NMR (360 MHz).$^1$ Anal. (C$_8$HNO$_3$) C, H, N.

N-Propionyl-L-Pro was coupled with 2 (26.4 mg, 0.028 mmol) as in the synthesis of 31 to give [propionyl$^9$] didemnin B (32) (28.7 mg, 93%) as a white powder: $^1$H NMR (CDCl$_3$, 500 MHz).$^1$ FABMS m/z 1097 (M+H), 281. HRFABMS: calcd for C$_{57}$H$_{90}$N$_7$O$_{14}$, M$_r$ 1096.6556 (M+H); found, 1096.6572.

[Isobutyryl$^9$]Didemnin B (33) and [Isobutyryl$^9$, D-Pro$^8$] Didemnin B (34). L-Pro (1.15 g, 0.01 mol) was treated with isobutyric anhydride in a procedure like the N-propionylproline synthesis to give N-isobutyrylproline (1.8 g, 96%): fine crystals, mp 80–82° C.; [α]$_D^{25}$ –8.7° (c 1.56, CHCl$_3$). $^1$H NMR Anal. (C$_9$H$_{15}$NO$_3$) C, H, N.

N-Isobutyrylproline was coupled with 2 (26.4 mg, 0.028 mmol) using the method described earlier for the preparation of 31. The product was separated (silica gel, EtOAc) to give 33 as the first fraction (8.7 mg, 28%), a white powder: $^1$H NMR (CDCl$_3$, 500 MHz) δ 8.11 (1H d, J=5.5), 7.89 (1H, d, J=9.0), 7.21 (1H, d, J=10.0), 7.06 (2H, d, J=8.5), 6.84 (2H, d, J=8.5), 3.79 (3H, s), 3.12 (3H, s), 2.54 (3H, s). FABMS m/z 1112 (M+H), 295. HRFABMS: calcd for C$_{58}$H$_{92}$N$_7$O$_{14}$, M$_r$ 1110.6302 (M+H); found, 1110.6737.

The second fraction gave 34 (13 mg, 42%), colorless needles: mp 162–164° C. $^1$H NMR (CDCl$_3$, 500 MHz) δ 9.15 (1H, d, J=6.0), 7.92*, 7.87* (1H, d, J=9.0), 7.26*, 7.11* (1H, d, J=10.0), 7.06 (1H, d, J=9.0), 6.94 (¼H, d, J=9.0), 6.84 (2H, d, J=8.5), 3.78 (3H, s), 2.86 (3H, s), 2.54, 2.53 (3H, s) (*peaks observed as pairs); FABMS m/z 1110 (M+H), 295. HRFABMS: calcd for C$_{58}$H$_{92}$N$_7$O$_{14}$, M$_r$ 1110.6302 (M+H); found, 1110.6726.

O-Benzyl-L-lactyl-L-Ala Methyl Ester. A mixture of O-benzyl-L-lactic acid$^{23}$ (57.7 mg, 0.35 mmol), L-alanine methyl ester hydrochloride (50.0 mg, 0.36 mmol), N-hydroxysuccinimide (82 mg, 0.70 mmol) and NMM (35 mg, 0.35 mmol) in CH$_2$Cl$_2$-DMF (6:4, 2 mL) was stirred at –10° C. A solution of DCC (100 mg, 0.49 mmol) and DMAP (2mg) in CH$_2$Cl$_2$-DMF (6:4,2 mL) was added to the mixture, which was allowed to warm from –10° C. to 4° C. over 2 h, then stood at 4° C. for 30 h. The reaction mixture was concentrated in vacuo, and the resulting product was suspended in cold EtOAc, filtered, and separated (silica gel, EtOAc) to give O-benzyl-Lactyl-L-Ala methyl ester as a light yellow oil (81.7 mg, 94%, HPLC data): [α]$_D^{20}$ –20° (c 1.2, CHCl$_3$). $^1$H NMR (CDCl$_3$, 300 MHz);$^1$ $^{13}$C NMR (CDCl$_3$, 75 MHz).$^1$ HRFABMS: calcd for C$_{14}$H$_{19}$NO$_4$, M$_r$ 266.1392 (M+H); found, 266.1 398.

O-Benzyl-L-lactyl-L-Ala. Aqueous KOH (1 N, 300 µL) was added to a solution of O-benzyl-L-lactyl-L-Ala methyl ester (62 mg, 0.25 mmol) in dioxane. The mixture was stirred for 12 h at rt, HCl (1 N, 300 µL) was added, and the solvent was removed in vacuo. The residue was suspended in CH$_2$Cl$_2$, filtered, and concentrated in vacuo to give O-benzyl-L-lactyl-L-Ala as a light yellow oil (56.9 mg, 98%): [α]$_D^{26}$ –18.8° (c 2.11, CHCl$_3$). $^1$H NMR (CDCl$_3$, 300 MHz).$^1$ HRFABMS: calcd for C13H$_{17}$N$_4$, M$_r$ 252.1236 (M+H); found, 252.1238.

O-Benzyl-[L-Ala$^8$] Didemnin B. A solution of O-benzyl-L-lactyl-L-Ala (22.6 mg, 0.095 mmol) and N-hydroxysuccinimide (13.1 mg, 1.2 mmol) in CH$_2$Cl$_2$ (1 mL) was added to a solution of DCC (21.5 mg, 0.10 mmol) in CH$_2$Cl$_2$ (0.5 mL) at –10° C. The mixture, which became a heterogeneous emulsion, was stirred for 1 h at –10° C. Compound 2 (81.4 mg, 0.086 mmol) and NNM (9.0 mg, 0.088 mmol) were added and the reaction mixture stood at –10° C. for 3 h then at 4° C. for 24 h. A catalytic amount of DMAP (1 mg) was added to the mixture, and the reaction stood for 16 h at 4° C., then was concentrated. The residue was suspended in EtOAc, filtered, and concentrated in vacuo to give an oil which was chromatographed on a silica gel column, eluting with CHCl$_3$—MeOH (15:1), to give O-benzyl-[L-Ala$^8$]didemnin B (62 mg, 62%) as a white powder: $^1$H NMR (300 MHz, CDCl$_3$).$^1$ FABMS m/z 1176 (M+H), 361. HRFABMS: calcd for C$_{62}$H$_{94}$N$_7$O$_{15}$, M$_r$ 1176.6808 (M+H); found, 1176.6814.

[L-Ala$^8$]Didemnin B (35). A mixture of O-benzyl-[L-Ala$^8$] didemnin B (53.2 mg, 0.045 mmol) and Pd/C (10%, 50 mg) in MeOH (2 mL, containing 100 µL of acetic acid) was vigorously stirred in an H$_2$ atmosphere for 3 h at rt. To the mixture was added 10 mg, of NaHCO$_3$, and the reaction mixture was filtered through a C-18 Sep-pak column with MeOH, and concentrated to give 35 (TLC, one spot; 47.6 mg, 97%). A portion of 35 was further purified for bioassay by HPLC (C-18, MeOH—H$_2$O, 7:1): IR (film) 3330, 1734, 1637, 1248 cm$^{-1}$; $^1$H NMR (CDCl$_3$, 500 MHz).$^1$ $^{13}$C NMR (CDCl$_3$, 300 MHz).$^1$ FABMS m/z 1087 (M+H), 271. HRFABMS: calcd for C$_{55}$H$_{88}$N$_7$O$_{15}$, M$_r$ 1086.6338 (M+H); found, 1086.6359.

O-Benzyl-L-lactyl-D-Pro Methyl Ester. A mixture of O-benzyl-L-lactic acid (194.4 mg, 1.08 mmol) and DCC (111.2 mg, 0.54 mmol) in CH$_2$Cl$_2$ (1 mL) was stirred at 0°

C. for 30 min. D-Pro-OMe-HCl (53.1 mg, 0.32 mmol) and NMM (33.0 mg, 0.33 mmol) in DMF (~1 mL) were added in the mixture stood at 4° C. for 9 h. The product was filtered, concentrated in vacuo, suspended in cold EtOAc, filtered, and concentrated in vacuo to an oil. The crude product was separated (silica gel, EtOAc) to give O-benzyl-L-lactyl-D-Pro methyl ester (47.6 mg, 44%) as a colorless oil: $[\alpha]_D^{26}$ +1.42° (c 1.83, CHCl$_3$); IR (film) 1736,1639, 1450, 1200, 1170 cm$^{-1}$; $^1$H NMR (CDCl$_3$, 500 MHz).$^1$ $_{13}$CNMR (CDCl$_3$, 300 MHz).$^1$ HRFABMS: calcd for $C_{16}H_{22}NO_4$, $M_r$ 292.1549 (M+H); found, 292.1550.

O-Benzyl-L-lactyl-D-Pro. A solution of O-benzyl-L-lactyl-D-Pro methyl ester (124.7 mg) in dioxane (1 mL) and aqueous KOH (1 N, 0.5 mL) stood at rt for 20 h. The mixture was concentrated to give an aqueous emulsion, which was acidified to pH 2 (HCl), extracted with CH$_2$Cl$_2$, dried (Na$_2$SO$_3$), and evaporated to give an oil (117.9 mg, 100%): IR (film) 3400–2500 br, 1736,16,40 cm$^{-1}$. HRFABMS: calcd for $C_{15}H_{20}NO_4$, $M^r$ 278.1392 (M+H); found, 278.1394.

O-Benzyl-[D-Pro$^8$]Didemnin B. A mixture of O-benzyl-L-lactyl-D-Pro (52.4 mg, 0.19 mmol) and DCC (19.6 mg, 0.095 mmol) in CH$_2$Cl$_2$ (1 mL) was stirred at 0° C. for 2 h. A solution of 2 (59.7 mg, 0.063 mmol) in CH$_2$Cl$_2$ (1 mL) was added and the reaction mixture was allowed to stand at 0° C. for 12 h, and concentrated in vacuo. The residue was suspended in EtOAc, and filtered, and the product was separated (silica gel, EtOAc) to give O-benzyl-[D-Pro$^8$] didemnin B (61.9 mg, 83% based on unreacted 2), as a white solid: $^1$H NMR (CDCl$_3$, 300 MHz) 6 7.94* (1H, d×2, 6.9, 6.3), 7.22–7.42 (5H, m), 7.13 (1H, d, J=9.9), 7.07 (2H, d, J=8.7), 6.95 (1H, d, J=9–0), 3.79 (3H, s), 2.95 and 2.88* (3H, s), 2.56 and 2.55* (3H, s) (*appearing as pairs of signals due to conformers). HRFABMS: calcd for $C_{64}H_{96}N_7O_{15}$, $M_r$ 1202.6664 (M+H); found, 1202.6671.

[D-Pro$^8$]Didemnin B (36). A mixture of O-benzyl-[D-Pro$^8$]-didemnin B (43.1 mg, 0.036 mmol) and Pd/C (10%, 40 mg) in MeOH (2 mL) and acetic acid (20 mL) was stirred under hydrogen for 2.5 h at rt. To the mixture was added 10 mg of NaHCO$_3$, and the product was filtered and concentrated in vacuo to a glass which was purified by HPLC (C-18, MeOH—H$_2$0, 7:1) to give pure 36 (39 mg, 97%) as a white powder: IR (film) 3420, 3330, 1732, 1635, 1539, 1248, 1176 cm$^{-1}$; $^1$H NMR (CDCl$_3$, 500 MHz, mixture of conformers, FIG. 1) δ 8.62:8.57 (3:1, ⅓H, (d's, J=6.5), 7.93, 7.92, 7.86, 7.83 (5:1:4:2, 1H, d's, J=9.5), 7.29:7.14 (1:1, 1H, d's, J=10.0), 7.07 (2H, d, J=8.5), 6.97:6.85 (1:4, 2/H, J=9.5), 6.84 (2H, d, J=8.5), 5.19:5.16 (2:3, 1H, d's, J=3.5, Hip H-4), 3.79 (3H, s, Me$_2$Tyr—OCH$_3$), 2.94:2.93:2.89:2.88 (5:2:4:1, 3H, singlets), 2.56:2.54 (2:3, 3H, singlets). HRFABMS: calcd for $C_{57}H_{90}N_7O_{15}$, Mr 1112.6491 (M+H); found, 1112.6493.

O-Pyroglutamyldidemnin B (37). A mixture of 1 (230 mg, 0.21 mmol), L-pyroglutamic acid (134 mg, 1.04 mmol) in DMF (5 mL), DCC (206 mg, 1.00 mmol) and DMAP (6 mg) was stirred for 20 h at rt. Water (50 mL) and CH$_2$Cl$_2$ (50 mL×3) were added to the reaction mixture, and the organic layer was concentrated in vacuo. The resulting solid was separated (silica gel column, EtOAc-2-propanol, 10:1) to give recovered 1 (77 mg, 33%) and 37 (135 mg, 53% conversion) as a white powder: IR (film) 3390, 1730, 1651, 1252 cm$^{-1}$; $^1$H NMR (300 MHz). FABMS: m/z 1224 (M+H), 1113, 447, 275, 195. HRFABMS: calcd for $C_{62}H_{95}N_8O_{17}$, $M_r$ 1223.6384 (M+H); found, 1223.6365.

Immunomodulating Activity

Mixed Lymphocyte Reaction (MLR)

Each compound was dissolved in absolute ethanol (abs. EtOH) and diluted 16-fold (from 10 µ/mL to 3.33×10$^{-6}$µg/mL). Duplicate volumes (10 µL) were added into wells of a 96-well microliter plate and then evaporated to dryness at room temperature. Splenocytes derived from Balb/c and C57B⅙ mice were prepared as described above, and 100µL of each cell suspension was added to each well. Wells containing 200 µL of media alone served as nonspecific control wells.

Assay plates were incubated in a 5% CO$_2$ humidified incubator at 37° C. for 96 h and then pulsed overnight (about 15 h) with 1 µCi of [$^3$H]thymidine (20 Ci/mmol) per well and finally filtered to recover tritiated-thymidine incorporated into newly synthesized DNA.

The MLR data were calculated as a percentage of immune cell proliferative activity relative to control, and an IC$_{50}$ value was interpolated for each test compound.

Lymphocyte Viability (LeV) Assay

Test compounds were prepared in two sets as described above. Splenocytes were prepared as described previously from one murine strain (Balb/c), and a volume of 200 µL of the cell suspension was added to one set of test compounds and control wells.

Assay plates were incubated as in the MLR and then pulsed overnight 75 µL per well MTT-thiazolyl blue solution (150 µg). The plates were decanted and the resulting insoluble formazan crystals were dissolved in 200 µL of isopropyl alcohol. Absorbance at 570 nm was measured.

The LcV data were calculated as a percentage of basal metabolic activity, or percent viability, relative to BALB/c control, and an LC$_{50}$ value was interpolated for each test compound.

Lymphoblast Viability (LbV) Assay

The cytotoxicity of didemnins and didemnin analogues on lymphoblasts was evaluated using a modification of the above LcV procedure. Mitogen-induced lymphoblastic proliferation was initiated by preincubation of splenocytes, as prepared above, with 1.0 µg/mL of concanavalin A (Con A) in a 5% CO$_2$ humidified incubator at 37° C. for 30 min. Test compounds were prepared as described above. Preincubated Con A splenocytes were added in a volume of 200 µL to each well. Incubation, processing, and data calculation were the same as described above for the LcV assay.

Graft vs. Host (GVH) Reaction

Three didemnins (didemnin B, didemnin M, and pGlu-didemnin B) were evaluated in a modified Simonsen splenomegaly assay. Briefly, an F1 hybrid host animal is grated with immunocompetent spleen cells from the parent strain. The index used to measure the success of the GVHR is splenomegaly (increased spleen weight due to cellular proliferation of grafted lymphocytes). An index>1.3 (graft index) is considered to be a successful graft rejection of the recipient animal. Immunosuppression is considered as a reduction of the graft index.

On day O, CB6F$_1$ female mice, 4 weeks of age, were grated by intraperitoneal (ip) injection of 50×10$^5$ splenocytes from BALB/c female mice in high-glucose (4500 mg/mL) Dulbecco's modified Eagles medium. A syngeneic control group (CB6F$_1$—CB6F$_1$) was similarly prepared and served as the negative control. Grafted mice were divided into treatment groups containing six mice each. Groups were injected ip with test compound (dissolved in vehicle; 1% abs. EtOH in sterile phosphate-buffered saline) at one of three dose levels (0.16, 0.016, and 0.0016 mg/kg per injection) in a multidose assay, cyclophosphamide (200 mg/kg per injection) or vehicle on days 1–7 (qd 1–7). On day 8 all groups were sacrificed, spleens were excised, and a graft index was calculated for each group by the following formula:

$$\text{graft index} = \frac{[(\text{spleen wt of test group})/(\text{body wt of test group}) \times 100]}{(\text{spleen wt of syngeneic group})/(\text{body wt of syngeneic group})}$$

INFORMATION DISCLOSURE

The following references have been cited herein:

1. R. Sakai, "Biologically Active Compounds from Tunicates and a Sponge," Ph.D. Thesis, University of Illinois, Urbana (1991)
2. K. L. Rinehart, Jr., "Pharmaceutical Compositions Containing Didemnins," U.S. Pat. No. 5,294,603, Mar. 15, 1994; *Chem. Abstr.*, (1994); 121,887.
3. (a) Rinehart et al., "Structures of the Didemnins, Antiviral and Cytotoxic Depsipeptides from a Caribbean Tunicate," *J. Am. Chem. Soc.*, 103, 1857–1859 (1981); (b) Rinehart et al., "Didemnins: Antiviral and Antitumor Depsipeptides from a Caribbean Tunicate," *Science*, 212, 933–935 (1981); (c) Rinehart et al., "Didemnins A, B, C, and Derivatives Thereof as Antiviral Agents," U.S. Pat. No. 4,493,796, Jan. 15, 1985; *Chem. Abstr.*, 103,7624lv, (1985); (d) K. L Rinehart, Jr., "Composition of Matter and Process," U.S. Pat. No. 4,548,81 4, Oct. 22, 1985.
4. (a) J. B. Gloer, "Structures of the Didemnins," Ph.D. Thesis, University of Illinois, Urbana, 1983; *Chem. Abstr.*, 101, 122692b (1984); *Diss. Abstr. Int.* B, 45, 188–189 (1984); (b) R. E. Gutowsky, "Isolation and Identification of Didemnins," M.S. Thesis, University of Illinois, Urbana, 1984.
5. Rinehart et al., "Biologically Active Peptides and Their Mass Spectra," *Pure Appl. Chem.*, 54, 2409–2424 (1982).
6. K. L. Rinehart, "Didemnin and Its Biological Properties," In Peptides, Chemistry and Biology; Proc. 10th Am. Peptide Symposium, G. R. Marshall Ed; ESCOM: Leiden, pp. 626–631 (1988) and references therein.
7. Rinehart et al., "Didemnins and Tunichlorin: Novel Natural Products From the Marine Tunicate *Trididemnum solidum*," *J. Nat Prod.*, 51, 1–21 (1988) and references therein.
8. V. Fimiani, "In Vivo Effect of Didemnin B on Two Tumors of the Rat," *Oncology*, 44, 42–46 (1987).
9. (a) National Cancer Institute Clinical Brochure, Didemnin B. NSC 325319. IND. Division of Cancer Treatment, NCl, Bethesda, MD, June 1984; (b) Chun et al., "Didemnin B: The First Marine Compound Entering Clinical Trials a an Antineoplastic Agent," *Invest. New Drugs*, 4, 279–284 (1986); (c) Dorr et al., "Phase I Clinical and Pharmacokinetic Investigation of Didemnin B, a Cyclic Depsipeptide," *Eur. J. Cancer Clin. Oncol.*, 24, 1699–1706 (1988); (d) Jones et al., "Phase II Study of Didemnin B in Advanced Colorectal Cancer," *Invest. New Drugs*, 15, 454–462 (1992); (f) Malfetano et al., "A Phase II Trial of Didemnin B (NSC #325319) in Patients with Previously Treated Epithelial Ovarian Cancer, A Gynecologic Oncology Group Study," *Am. J. Clin. Oncol.*, 16, 47–49 (1993).
10. Annual Report to the Food and Drug Administration. Didemnin B. NSC 35319. IND 24505 Division of Cancer Treatment, NCl, Bethesda, Md, August 1994.
11. (a) Li et al., "Mechanism of Action of Didemnin B, a Depsipeptide from the Sea," *Cancer Lett.*, 23, 279–288 (1984); (b) Crews et al., "GTP-dependent Binding of the Antiproliferative Agent Didemnin to Elongation Factor 1 alpha," *J. Biol Chem.*, 269, 1541–15414 (1994); (c) SirDeshpande et al., "Mechanism of Protein-Synthesis Inhibition by Didemnin B in vitro," *Biochemistry*, 34, 9177–9184 (1995); (d) Grubb et al., "Didemnin-B Induces Cell-Death by apoptosis—The Fastest Induction of Apoptosis Ever Described," *Biochem. Biophys. Res. Commun.*, 215, 1130–1136 (1995).
12. Weed et al., "Didemnins A and B, Effectiveness Against Cutaneous Herpes simplex Virus in Mice," *Antiviral Res.*, 3, 269–274 (1983).
13. Canonico et al., "Inhibition of RNA Viruses in vitro and in Rift Valley Fever-Infected Mice by Didemnins A and B," *Antimicrob. Agents Chemother.*, 22, 696–697 (1982).
14. Montgomery et al., "Didemnin B: A New Immunosuppressive Cyclic Peptide with Potent Activity in vitro and in vivo," *Transplantation*, 40, 49–56 (1985).
15. Montgomery et al., "Didemnin B: An Immunosuppressive Cyclic Peptide that Stimulates Murine Hemagglutinating Antibody Responses and Induces Leukocytosis In Vivo," *Transplantation*, 43, 133–139 (1987).
16. Yuh et al., "Efficacy of Didemnin B Therapy in Prolonging Cardiac Allograft Survival in Mice and Rats," *FASEB J.*, 2, Abstract 9006 (1988).
17. Jouin et al., "Antineoplastic Activity of Didemnin Congeners: Nordidemnin and Modified Chain Analogues," *J. Med. Chem.*, 34, 486–491 (1991).
18. Kessler et al., "Solution Structure of [Me-L-Leu$^7$] Didemnin B Determined by NMR Spectroscopy and Refined by MD Calculation," *Helv. Chim. Acta*, 73, 25–47 (1990).
19. Mayer et al., "Synthesis of New Didemnin B Analogs for Investigation of Structure/Biological Activity Relationships," *J. Org. Chem.* 59, 5192–5205 (1994).
20. (a) Sakai et al., "Seven New Didemnins from the Marine Tunicate Trididemnum solidum," *J. Am. Chem. Soc.*, 117, 3734–3748 (1995); (b) K. L. Rinehart, "Pharmaceutical Compositions Containing Didemnins," U.S. Pat. 5,294,604, Mar. 15, 1994; *Chem. Abstr.*, 121, P887m (1994).
21. Rinehart et al., "Novel Antiviral and Cytotoxic Agent," PCT *Int. Pat. Appl.* WO91/04985, Apr. 18, 1991; GB Appl. 89/22,026, Sep. 29, 1989, *Chem. Abstr.*, 115, 248086q (1991).
22. Rinehart et al., "Synthesis and Properties of the Eight Isostatine Stereoisomers," *J. Org. Chem.*, 57, 3007–3013 (1992).
23. Rinehart et al., "Total Synthesis of Didemnins A, B, and C," *J. Am. Chem. Soc.*, 109, 6846–6848 (1987).
24. Mitsunobu, "The Use of Diethyl Azodicarboxylate and Triphenylphosphine in Synthesis and Transformation of Natural Products," *Synthesis*, 1–28 (1981).
25. Didemnin M was also recently reported by Boulanger et al., under the name didemnin H. ["The Complete Spectral Assignment of Didemnin H, a New Constituent of the Tunicate *Trididemnum cyanophorum*," *Tetrahedron Lett*, 25, 4345–4348 (1994)] In view of Rinehart's earlier use of the name didemnin H for a different didemnin (M+H=957, tentatively N-alpha-formyl-N-alpha-demethyl didemnin A [4b]) and didemnin M for the present compound[1,20], the previous nomenclature is being retained herein.

26. (a) Bergeron et al., "Antineoplastic and Antiherpetic Activity of Spermidine Catecholamide Iron Chelators," *Biochem. Biophys. Res. Commun.*, 121, 848–854 (1984); (b) Schroeder et al., "Synthesis and Biological Effects of Acyclic Pyrimidine Nucleoside Analogues," *J. Med Chem.*, 24, 1078–1083 (1981).

27. Tomita et al., "A Novel Antitumor Antibiotic. 3. Mode of Action," *J. Antibiot.*, 37, 1268–1272 (1984).

28. Spadari et al., "DNA Polymerases and DNA Topoisomerases as Targets for the Development of Anticancer Drugs," *Anticancer Res.*, 6, 935–940 (1986).

29. Hsiang et al., "Camptothecin Induces Protein-linked DNA Breaks via Mammalian DNA Topoisomerase I," *J. Biol. Chem.*, 260, 14873–14878 (1985).

30. Baccanari et al., "Inhibition of Dihydrofolate Reductase: Effect of Reduced Nicotinamide Adenine Dinucleotide Phosphate of the Selectivity and Affinity of Diaminobenzylpyrimidines," *Biochemistry*, 21, 5068–5075 (1982).

31. Dunlap et al., "Thymidylate Synthetase from Amethopterin-Resistant *Lactobacillus casei,*" *Biochemistry*, 10, 88–97 (1971).

32. R. P. Agarwal, "Inhibitors of Adenosine Deaminase," *Pharmacol. Ther.*, 17, 399–429 (1982).

33. Simpson et al., "Analysis of Cytotoxic T Cell Responses," In Volume 2: Cellular Immunology, Weir, D. M., Ed; Blackwell Scientific Publications: Boston, Chapter 68 (1986).

34. Hossain et al., "Crystal and Molecular Structure of Didemnin B, an Antiviral and Cytotoxic Depsipeptide," *Proc. Nat. Acad. Sci. U.S.A.*, 85, 4118–4122 (1988).

35. Kessler et al., "Conformational Analysis of Didemnins. A Multidisciplinary Approach by Means of X-Ray, NMR, Molecular-Dynamics, and Molecular-Mechanics Techniques," *Helv. Chim. Acta*, 72, 530–555 (1989).

36. Lagrue et al., "Inhibition of T-Lymphocyte Proliferation by the Cyclic Polypeptide Didemnin B: No Inhibition of Lymphokine Stimulation," *Lymphokine Res.*, 7, 21–29 (1988).

37. Rosen et al., "Natural Products as Probes of Cellular Function: Studies of Immunophilins," *Angew. Chem. Int. Ed. Engl.*, 31, 384–400 (1992).

38. S. L. Schreiber, "Chemistry and Biology of the Immunophilins and Their Immunosuppressive Ligands," *Science*, 251, 283–287 (1991).

39. Schendel et al., "The Involvement of LD- and SD-Region Differences in MLC and CML: A Three-Cell Experiment," *Transplant. Proc.*, 5, 1651–1655 (1973).

40. Faircloth et al., "A Simple Screening Procedure for the Quantitative Measurement of Cytotoxicity to Resting Primary Lymphocyte Cultures," *J. Tissue Cult. Meth.*, 11, 201–205 (1988).

41. L. M. Bradley, "Mitogen-Induced Responses," In Selected Methods in Cellular Immunology; Mishell, B. G; Shiigi, S. M., Eds.; W. H. Freeman; San Francisco, Chapter 6.2, pp. 156–161 (1980).

42. M. Simonsen, "Graft Versus Host Reactions: Their History and Applicability as Tools of Research," *Progr. Allergy*, 6, 349–467 (1962).

43. In Beilsteins Handbuch der Organischen Chemie: Luckenbach, R., Ed.; Springer-Verlag: Berlin, Vol. 22, p. 30 (1979).

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A method of suppressing an immune system in a subject in need thereof, which comprises the administration to the subject an immune system suppressing amount of an immunosuppressant didemnin compound selected from the group consisting of: Didemnin M, O-pGlu-Didemnin B, Didemnin E and mixtures thereof, in a pharmaceutically acceptable carrier or diluent.

2. The method of claim 1, in which the immune system disorder is selected from the group consisting of soft tissue destruction due to burn, myocardial infarct induced trauma, adult respiratory distress syndrome, and myocardial ischemia and re-perfusion; specific and non-specific proteolytic processing of C5; inflammation associated with kidney stones, systemic lupus erythematosus, nephrotoxic glomeronephritis, and multiple sclerosis; atrophic gastritis, thyroiditis, allergic encephalomyelitis, gastric mucosa, thyrotoxicosis, autoimmune hemolytic anemia, pemphigus vulgaris, sympathetic ophthalmia, delayed-type hypersensitivity, autoimmune disorders and drug allergies; and tissue plasminogen activator therapy and cardiopulmonary bypass.

3. A method for treating a mammal in need of immunosuppression, comprising systemically administering to the mammal an effective amount of an immunosuppressant didemnin compound selected from the group consisting of Didemnin M, O-pGlu-Didemnin B, Didemnin E and mixtures thereof, in a pharmaceutically-acceptable diluent or carrier.

4. A method of promoting immunosuppression in a mammal, comprising systemically administering to the mammal an effective amount of an immunosuppressant didemnin compound selected from the group consisting of Didemnin M, O-pGlu-Didemnin B, Didemnin E and mixtures thereof, in a pharmaceutically-acceptable diluent or carrier.

* * * * *